United States Patent
Tsuchiya et al.

(10) Patent No.: US 7,067,297 B2
(45) Date of Patent: Jun. 27, 2006

(54) MANNOSYLTRANSFERASE POLYPEPTIDES AND POLYNUCLEOTIDES ENCODING THEM AND METHODS FOR MAKING AND USING THEM

(75) Inventors: Masayuki Tsuchiya, Shizuoka (JP); Mikiyoshi Saito, Shizuoka (JP); Hirotaka Ito, Shizuoka (JP); Motooki Ashihara, Shizuoka (JP); Toshihiko Ohtomo, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/204,033

(22) PCT Filed: Feb. 15, 2001

(86) PCT No.: PCT/JP01/01083

§ 371 (c)(1),
(2), (4) Date: Dec. 9, 2002

(87) PCT Pub. No.: WO01/61004

PCT Pub. Date: Aug. 23, 2001

(65) Prior Publication Data

US 2003/0138802 A1    Jul. 24, 2003

(30) Foreign Application Priority Data

Feb. 15, 2000    (JP) ............... 2000-041459

(51) Int. Cl.
| C12P 21/06 | (2006.01) |
| C12N 9/00 | (2006.01) |
| C12N 9/10 | (2006.01) |
| C12N 12/06 | (2006.01) |
| C07H 21/04 | (2006.01) |

(52) U.S. Cl. .................. 435/193; 435/4; 435/69.1; 435/183; 435/252.3; 435/320.1; 536/23.2; 536/23.4; 536/23.5; 536/23.7; 530/350

(58) Field of Classification Search ............ 435/4, 435/6, 69–1, 183 T, 193, 194, 200 T, 252–3 T, 435/320.1, 325; 530/350; 536/23.2, 23.4, 536/23.5, 24.31 T
See application file for complete search history.

(56) References Cited

U.S. PATENT DOCUMENTS

| 6,590,075 B1 * | 7/2003 | Ruben et al. ............... 530/350 |
| 2003/0008348 A1 * | 1/2003 | Desnoyers et al ......... 435/69.1 |
| 2003/0027272 A1 * | 2/2003 | Baker et al. .............. 435/69.1 |

FOREIGN PATENT DOCUMENTS

| WO | WO 96/01843 | 1/1996 |
| WO | WO 98/39446 | 9/1998 |
| WO | WO 00/56889 | 9/2000 |

OTHER PUBLICATIONS

Fukuda et al. (BBRC, Jan. 2001, vol. 280(1):407-414 and PIR database accession No. JC587.*
Hamada et al. (Gene, 1996, vol. 176:211-214, cited in the IDS, also see enclosed sequence alignment with PIR accession No. JC5105.*
Kalnine N et al. SPTREMBL accession No. Q86U75, Jun. 2003.*
Dunham et al., Nature 402(6761):489-495 (1999).
Fukuda et al., Biochem. Biophys. Res. Commun. 280(1)407-414 (2001).
Lussier et al., J. Biol. Chem. 270(6):2770-2775 (1995).
Shimizu, EMBL Accession No. AP000553 (Sep. 29, 1999).
Strahl-Bolsinger et al., Proc. Natl. Acad. Sci. U.S.A. 90(17):8164-8168 (1993).
Strausberg, EMBL Accession No. AI739099 (Jun. 23, 1999).
Strausberg, EMBL Accession No. AI638546 (Apr. 29, 1999).
Supplementary European Search Report mailed on Apr. 6, 2004 for EP 01904475, 6 pages.
Hamada et al. "Isolation and Characterization of a Novel Secretory Protein, Stromal Cell-Derived Factor-2(SDF-2) Using the Sequence Trap Method" Gene 176(1-2):211-214 (1996).

\* cited by examiner

Primary Examiner—Manjunath N. Rao
(74) Attorney, Agent, or Firm—Morrison & Foerster LLP

(57) ABSTRACT

A DNA encoding a novel protein SMAP-1 having a signal sequence was successfully isolated by screening a cDNA library derived from human fetal hepatocyte using the TMT method developed originally by the inventors. Based on the expression pattern and structural properties, SMAP-1 was suggested to be a molecule playing an important role in living cells.

8 Claims, 5 Drawing Sheets

```
         10        20        30        40        50        60
CGAGGGGCTGGAGCCGGGCCGGGGCGATGTGGAGCGCGGGCCGCGGCGGGGCTGCCTGGC
                              MetTrpSerAlaGlyArgGlyGlyAlaAlaTrpPro
                              *1
         70        80        90       100       110       120
CGGTGCTGTTGGGGCTGCTGCTGGCGCTGTTAGTGCCGGGCGGTGGTGCCGCCAAGACCG
  ValLeuLeuGlyLeuLeuLeuAlaLeuLeuValProGlyGlyGlyAlaAlaLysThrGly
        130       140       150       160       170       180
GTGCGGAGCTCGTGACCTGCGGGTCGGTGCTGAAGCTGCTCAATACGCACCACCGCGTGC
  AlaGluLeuValThrCysGlySerValLeuLysLeuLeuAsnThrHisHisArgValArg
        190       200       210       220       230       240
GGCTGCACTCGCACGACATCAAATACGGATCCGGCAGCGGCCAGCAATCGGTGACCGGCG
  LeuHisSerHisAspIleLysTyrGlySerGlySerGlyGlnSerValThrGlyVal
        250       260       270       280       290       300
TAGAGGCGTCGGACGACGCCAATAGCTACTGGCGGATCCGCGGCGGCTCGGAGGGCGGGT
  GluAlaSerAspAspAlaAsnSerTyrTrpArgIleArgGlyGlySerGlyGlyGlyCys
        310       320       330       340       350       360
GCCCGCGCGGGTCCCCGGTGCGCTGCGGGCAGGCGGTGAGGCTCACGCATGTGCTTACGG
  ProArgGlySerProValArgCysGlyGlnAlaValArgLeuThrHisValLeuThrGly
        370       380       390       400       410       420
GCAAGAACCTGCACACGCACCACTTCCCGTCGCCGCTGTCCAACAACCAGGAGGTGAGTG
  LysAsnLeuHisThrHisHisPheProSerProLeuSerAsnAsnGlnGluValSerAla
        430       440       450       460       470       480
CCTTTGGGGAAGACGGCGAGGGCGACGACCTGGACCTATGGACAGTGCGCTGCTCTGGAC
  PheGlyGluAspGlyGluGlyAspAspLeuAspLeuTrpThrValArgCysSerGlyGln
        490       500       510       520       530       540
AGCACTGGGAGCGTGAGGCTGCTGTGCGCTTCCAGCATGTGGGCACCTCTGTGTTCCTGT
  HisTrpGluArgGluAlaAlaValArgPheGlnHisValGlyThrSerValPheLeuSer
        550       560       570       580       590       600
CAGTCACGGGTGAGCAGTATGGAAGCCCCATCCGTGGGCAGCATGAGGTCCACGGCATGC
  ValThrGlyGluGlnTyrGlySerProIleArgGlyGlnHisGluValHisGlyMetPro
        610       620       630       640       650       660
CCAGTGCCAACACGCACAATACGTGGAAGGCCATGGAAGGCATCTTCATCAAGCCTAGTG
  SerAlaAsnThrHisAsnThrTrpLysAlaMetGluGlyIlePheIleLysProSerVal
        670       680       690       700       710       720
TGGAGCCCTCTGCAGGTCACGATGAACTCTGAGTGTGTGGATGGATGGGTGGATGGAGGG
  GluProSerAlaGlyHisAspGluLeu***    (SEQ ID NO:2)
        730       740       750       760       770       780
TGGCAGGTGGGGCGTCTGCAGGGCCACTCTTGGCAGAGACTTTGGGTTTGTAGGGGTCCT
        790       800       810       820       830       840
CAAGTGCCTTTGTGATTAAAGAATGTTGGTCTATGAAAAAAAAAAAAAAAAAAAAAAAAA
        850       860       870
AAAAAAAAAAAAAAAAAAAAAAAAAAAAAA    (SEQ ID NO:1)
```

Figure 1

```
SMAP-1    1 : CGAGGGGCTG GAGCCGGGCC GGGGCGATGT GGAGC-GCGG GCCGCGGCGG GGCTGCCTGG
               * *         *        *  *** *  ** ** **  *  * **     ** ** ***
SDF-2     1 : ———————GTT- ——————TTCT TCGAAGATTT GGGGCTCCGC GATACAGTTA GGATGGCTG-

SMAP-1   60 : CCGGTGCTGT TGGGGCTGCT GCTGGCGCTG TTAGTGCCGG GCGGTGGTGC CGCCAAGACC
               ** *       *   **** * * *** *  * ** ***  *   ** ****   ** * ** **
SDF-2    47 : -TAGTACCTC T——-GCTGTT GTTGG-GGGG TTTGTGGAGC GCTGTGGGAG CGTCCAG-CC

SMAP-1  120 : GGTGCGGAGC TCGTGACCTG CGGGTCGGTG CTGAAGCTGC TCAATACGCA CCACCGCGTG
               ** ** *    ***** ** *** ** *** ******* * ********* ****    ***
SDF-2   101 : —-TG-GGTG- TCGTTACTTG CGGCTCCGTG GTGAAGCTAC TCAATACGCG CCACAACGTC

SMAP-1  180 : CGGCTGCACT CGCACGACAT CAAATACGGA TCCGGCAGCG GCCAGCAATC GGTGACCGGC
               ** *******  * ****** *          ** **    ** * ** * ***** **   ***** **
SDF-2   157 : CGACTGCACT CACACGACGT GCGCTATGGG TCAAGTAGTG GGCAGCAGTC AGTGACAGGT

SMAP-1  240 : GTAGAGGCGT CGGACGACGC CAATAGCTAC TGGCGGATCC GCGGCGGCTC GGAGGGC———
               ***     *  *** ***   *** ** ***   ***** **    ******      *** **
SDF-2   217 : GTAACCTCTG TGGATGACAG CAACAGTTAC TGGAGGAT— ACGGCGG-—A AGAGTGCCAC

SMAP-1  297 : -GGGTGCCCG CGCGGGTCCC CGGTGCGCTG CGGGCAGGCG GTGAGGCTCA CGCATGTGCT
               * ***      *  * ***   *** *  *      **    ** ** ***  *    * **** * * *****
SDF-2   273 : AGTGTGTGAG AGGGGAACCC CCATCAAGTG TGGCCAGCCC ATCCGGCTGA CACATGTCAA

SMAP-1  356 : TACGGGCAAG AACCTGCACA CGCACCACTT CCCGTCGCCG CTGTCCAACA ACCAGGAGGT
               ** ***     ****  ** *  ********* * *** **   ** **   *  * ******* **
SDF-2   333 : CACTGGCCGA AACCTCCATA GTCACCACTT CACTTCACCT CTTTCTGGAA ACCAGGAAGT

SMAP-1  416 : GAGTGCCTTT GGGGAAGACG GCGAGGGCGA CGACCTGGAC CTATGGACAG TGCGCTGCTC
               ** ***  *** ** ***** * * ** ** **   * ****    ******* *** ***
SDF-2   393 : GACTGCTTTT GGTGAAGAAG GTGAAGGTGA TTATCTGGAT GACTGGACAG TGCTCTGTAA

SMAP-1  476 : TGGACAGCAC TGGGAGCGTG AGGCTGCTGT GCGCTTCCAG CATGTGGGCA CCTCTGTGTT
               *****      **  ****** * *  *  *** *** *** *  **        ** *   ** *
SDF-2   453 : TGGACCCTAC TGGGTGAGAG ATGGTGAGGT GCGGTTCAAA CACTCTTCCA CTGAGGTACT

SMAP-1  536 : CCTGTCAGTC ACGGGTGAGC AGTATGGAAG CCCCATCCGT GGGCAGCATG AGGTCCACGG
               *****  ***  ** ** ** *  ***** *    ** *** **  *****  * * **** ** **
SDF-2   513 : GCTGTCTGTC ACAGGAGAAC AATATGGTCG ACCTATCAGT GGGCAAAAAG AGGTGCATGG

SMAP-1  596 : CAT-GCCCAG TGCCAACAC- GCACAA-TAC GTGGAAGGCC ATGGAAGGCA TCTTCATCAA
               *** *****    *****   *  * **** ***  ***** *** ********** ******* **
SDF-2   573 : CATGGCCCA— -GCCAAGTCA GAACAACTAC -TGGAAAGCC ATGGAAGGCA TCTTCATGAA

SMAP-1  653 : GCCTAGTG——  —————————  -TGGAGCCCT C—TGCAG——   ————————   ————————
               *** ****               * *****   * *****
SDF-2   630 : GCCCAGTGAG TTGTTGAAGG CAGAAGCCCA CCATGCAGAG CTGTGAATCT TGAGGCTCTG

SMAP-1   (SEQ ID NO:1)

SDF-2    (SEQ ID NO:3)
```

Figure 2

```
SMAP-1   676 : ----------GT- ----CACGAT GAACTCTGA- GTGTGTGGAT ---------- -GGA-------
                          **  *** **  *  *  * **  * *** * *             ***
SDF-2    690 : AGGCACTGTT AACGCACAAT GTTCACAGAC ATCTGTTGCT GCCTCACCTT GGGATCCCTG

SMAP-1   706 : ---------- -TGGG----- ---------- ----TG-GAT G--------- -----GAG--
                             ****                      ** *** *              ***
SDF-2    750 : CCACAAGTTC CTTGGGCAGT GGCCATGTCA CCATTGAGAT GAAGATATAC AACAGAGAAA

SMAP-1   719 : -GGTGGCAG- ---GTGGG---G CGTCTGCAGG GC-CACT--- ---CTTGGCA- ------GAGAC
                ***** *      ****  * ** **  ** ** *       ** * **          ****
SDF-2    810 : TAGTGGCTGT GTTTGGGAAG CTTCAGCCCT GCACATTTTG AACTAGTCAC TCTCCCAGAC

SMAP-1   761 : TT-------TGG G-------TT T----GTAG GGG---TCCT ---------- -CAAGTGCCT
                **         ***  *         **  *    ****  **   * **                ** *** *
SDF-2    870 : TTGGCGGTGG GTCAGTTCTT TCCTGAGTAG AGGACTTGCT GGTAAAAGGG GCAGATGCTT

SMAP-1   790 : TT-------- GTGATTAAA- ---------- ---------- ---------- GAA--TGT--
                **         ********                                      *** ***
SDF-2    930 : TTTATTAGTA CTGATTAAAC CACACTGAGG GAAACATCCC TCTTAGCTGG GAAACTGTTT

SMAP-1   807 : ---------- ---------- -TGG------ ---------- ---------- --------TC
                                       ***                                     **
SDF-2    990 : ACTCTTCAGG AGCTTGGCAT CATGGACTGT TAATGTATGT GATTTTCCCC CTATTTTCTC

SMAP-1   812 : T-------A TGA------- ---------- ---AA   (SEQ ID NO:1)
                *        *  ***                      *
SDF-2   1050 : TCCCCCACAA TGATAAAAAC AATAATTTTA TTATGA  (SEQ ID NO:3)
Matching      :   50.09 [%]
```

Figure 3

```
SMAP-1    1 : MWSAGRGGAA WPVLLGLLLA LLVPGGGAAK TGAELVTCGS VLKLLNTHHR VRLHSHDIKY
              *          *    ***   *       **  *   ***** * ***** *  ******* *
SDF-2     1 : M--------- -AVVPLLLLG GLWSAVGASS LG--VVTCGS VVKLLNTRHN VRLHSHDVRY

SMAP-1   61 : GSGSGQQSVT GVEASDDANS YWRIRGGSEG GCPRGSPVRC GQAVRLTHVL TGKNLHTHHF
              ** *******  **    ** ** *****   *   * ** *   ** **** ** *** ***
SDF-2    49 : GSSSGQQSVT GVTSVDDSNS YWRIRRKSAT VCERGTPIKC GQPIRLTHVN TGRNLHSHHF

SMAP-1  121 : PSPLSNNQEV SAFGEDGEGD DLDLWTVRCS GQHWEREAAV RFQHVGTSVF LSVTGEQYGS
              **** ****  **** **** ** *** *  *  * *    * ** *  * *  **********
SDF-2   109 : TSPLSGNQEV TAFGEEGEGD YLDDWTVLCN GPYWVRDGEV RFKHSSTEVL LSVTGEQYGR

SMAP-1  181 : PIRGQHEVHG MPSANTHNTW KAMEGIFIKP S--VEPSAGH DEL  (SEQ ID NO:2)
              ** ** **** *      * * ******* ** *    * *   *
SDF-2   169 : PISGQKEVHG MAQPSQNNYW KAMEGIFMKP SELLKAEAHH AEJ  (SEQ ID NO:4)
                          Matching      :   60.09 [%]
J: stop code
```

Figure 4

SEQUENCE LISTING

```
<160> NUMBER OF SEQ ID NOS: 9

<210> SEQ ID NO 1
<211> LENGTH: 870
<212> TYPE: DNA
<213> ORGANISM: Homo sapiens
<220> FEATURE:
<221> NAME/KEY: CDS
<222> LOCATION: (27)..(689)

<400> SEQUENCE: 1
cgaggggctg gagccgggcc ggggcg atg tgg agc gcg ggc cgc ggc ggg gct        53
                            Met Trp Ser Ala Gly Arg Gly Gly Ala
                             1               5 gcc tgg ccg gtg ctg ttg ggg ctg ctg ctg gcg ctg tta gtg ccg ggc        101
Ala Trp Pro Val Leu Leu Gly Leu Leu Leu Ala Leu Leu Val Pro Gly
 10              15                  20                  25 ggt ggc gcc gcc aag acc ggt gcg gag ctc gtg acc tgc ggg tcg gtg        149
Gly Gly Ala Ala Lys Thr Gly Ala Glu Leu Val Thr Cys Gly Ser Val
             30                  35                  40 ctg aag ctg ctc aat acg cac cac cgc gtg cgg ctg cac tcg cac gac        197
Leu Lys Leu Leu Asn Thr His His Arg Val Arg Leu His Ser His Asp
         45                  50                  55 atc aaa tac gga tcc ggc agc ggc cag caa tcg gtg acc ggc gta gag        245
Ile Lys Tyr Gly Ser Gly Ser Gly Gln Gln Ser Val Thr Gly Val Glu
     60                  65                  70 gcg tcg gac gac gcc aat agc tac tgg cgg atc cgc ggc ggc tcg gag        293
Ala Ser Asp Asp Ala Asn Ser Tyr Trp Arg Ile Arg Gly Gly Ser Glu
```

|     |     |     |     |     |     |     |     |     |     |     |     |     |     |     |     |
| --- | --- | --- | --- | --- | --- | --- | --- | --- | --- | --- | --- | --- | --- | --- | --- |
|     |     |     |     | 75  |     |     |     |     | 80  |     |     |     |     | 85  |     |

```
ggc ggg tgc ccg cgc ggg tcc ccg gtg cgc tgc ggg cag gcg gtg agg      341
Gly Gly Cys Pro Arg Gly Ser Pro Val Arg Cys Gly Gln Ala Val Arg
 90              95                 100                 105 ctc acg cat gtg ctt acg ggc aag aac ctg cac acg cac cac ttc ccg      389
Leu Thr His Val Leu Thr Gly Lys Asn Leu His Thr His His Phe Pro
                110                 115                 120 tcg ccg ctg tcc aac aac cag gag gtg agt gcc ttt ggg gaa gac ggc      437
Ser Pro Leu Ser Asn Asn Gln Glu Val Ser Ala Phe Gly Glu Asp Gly
            125                 130                 135 gag ggc gac gac ctg gac cta tgg aca gtg cgc tgc tct gga cag cac      485
Glu Gly Asp Asp Leu Asp Leu Trp Thr Val Arg Cys Ser Gly Gln His
        140                 145                 150 tgg gag cgt gag gct gct gtg cgc ttc cag cat gtg ggc acc tct gtg      533
Trp Glu Arg Glu Ala Ala Val Arg Phe Gln His Val Gly Thr Ser Val
    155                 160                 165 ttc ctg tca gtc acg ggt gag cag tat gga agc ccc atc cgt ggg cag      581
Phe Leu Ser Val Thr Gly Glu Gln Tyr Gly Ser Pro Ile Arg Gly Gln
170                 175                 180                 185 cat gag gtc cac ggc atg ccc agt gcc aac acg cac aat acg tgg aag      629
His Glu Val His Gly Met Pro Ser Ala Asn Thr His Asn Thr Trp Lys
                190                 195                 200 gcc atg gaa ggc atc ttc atc aag cct agt gtg gag ccc tct gca ggt      677
Ala Met Glu Gly Ile Phe Ile Lys Pro Ser Val Glu Pro Ser Ala Gly
            205                 210                 215 cac gat gaa ctc tgagtgtgtg gatggatggg tggatggagg gtggcaggtg          729
His Asp Glu Leu
            220 gggcgtctgc agggccactc ttggcagaga ctttgggttt gtaggggtcc tcaagtgcct    789 ttgtgattaa agaatgttgg tctatgaaaa aaaaaaaaaa aaaaaaaaaa aaaaaaaaaa    849 aaaaaaaaaa aaaaaaaaaa a                                              870
```

<210> SEQ ID NO 2
<211> LENGTH: 221
<212> TYPE: PRT
<213> ORGANISM: Homo sapiens

<400> SEQUENCE: 2

```
Met Trp Ser Ala Gly Arg Gly Gly Ala Ala Trp Pro Val Leu Leu Gly
 1               5                  10                  15

Leu Leu Leu Ala Leu Leu Val Pro Gly Gly Ala Ala Lys Thr Gly
            20                  25                  30

Ala Glu Leu Val Thr Cys Gly Ser Val Leu Lys Leu Leu Asn Thr His
        35                  40                  45

His Arg Val Arg Leu His Ser His Asp Ile Lys Tyr Gly Ser Gly Ser
    50                  55                  60

Gly Gln Gln Ser Val Thr Gly Val Glu Ala Ser Asp Ala Asn Ser
 65                  70                  75                  80

Tyr Trp Arg Ile Arg Gly Gly Ser Glu Gly Gly Cys Pro Arg Gly Ser
                85                  90                  95

Pro Val Arg Cys Gly Gln Ala Val Arg Leu Thr His Val Leu Thr Gly
                100                 105                 110

Lys Asn Leu His Thr His His Phe Pro Ser Pro Leu Ser Asn Asn Gln
            115                 120                 125

Glu Val Ser Ala Phe Gly Glu Asp Gly Glu Gly Asp Asp Leu Asp Leu
        130                 135                 140
```

```
Trp Thr Val Arg Cys Ser Gly Gln His Trp Glu Arg Glu Ala Ala Val
145                 150                 155                 160

Arg Phe Gln His Val Gly Thr Ser Val Phe Leu Ser Val Thr Gly Glu
                165                 170                 175

Gln Tyr Gly Ser Pro Ile Arg Gly Gln His Glu Val His Gly Met Pro
            180                 185                 190

Ser Ala Asn Thr His Asn Thr Trp Lys Ala Met Glu Gly Ile Phe Ile
            195                 200                 205

Lys Pro Ser Val Glu Pro Ser Ala Gly His Asp Glu Leu
210                 215                 220
```

<210> SEQ ID NO 3
<211> LENGTH: 1085
<212> TYPE: DNA
<213> ORGANISM: Homo sapiens

<400> SEQUENCE: 3

```
gttttcttcg aagatttggg gctccgcgat acagttagga tggctgtagt acctctgctg     60
ttgttggggg gtttgtggag cgctgtggga gcgtccagcc tgggtgtcgt tacttgcggc    120
tccgtggtga agctactcaa tacgcgccac aacgtccgac tgcactcaca cgacgtgcgc    180
tatgggtcaa gtagtgggca gcagtcagtg acaggtgtaa cctctgtgga tgacagcaac    240
agttactgga ggatacggcg aagagtgcca cagtgtgtg agaggggaac ccccatcaag    300
tgtggccagc ccatccggct gacacatgtc aacactggcc gaaacctcca tagtcaccac    360
ttcacttcac ctctttctgg aaaccaggaa gtgactgctt tggtgaaga aggtgaaggt    420
gattatctgg atgactggac agtgctctgt aatggaccct actgggtgag agatggtgag    480
gtgcggttca acactcttc cactgaggta ctgctgtctg tcacaggaga acaatatggt    540
cgacctatca gtgggcaaaa agaggtgcat ggcatggccc agccaagtca gaacaactac    600
tggaaagcca tggaaggcat cttcatgaag cccagtgagt tgttgaaggc agaagcccac    660
catgcagagc tgtgaatctt gaggctctga ggcactgtta acgcacaatg ttcacagaca    720
tctgttgctg cctcaccttg gatccctgc acaagttcc ttgggcagtg gccatgtcac    780
cattgagatg aagatataca acagagaaat agtggctgtg tttgggaagc ttcagccctg    840
cacattttga actagtcact ctcccagact tggcggtggg tcagttcttt cctgagtaga    900
ggacttgctg gtaaaagggg cagatgcttt ttattagtac tgattaaacc acactgaggg    960
aaacatccct cttagctggg aaactgttta ctcttcagga gcttggcatc atggactgtt   1020
aatgtatgtg attttccccc tatttctct cccccacaat gataaaaaca ataattttat   1080
tatga                                                               1085
```

<210> SEQ ID NO 4
<211> LENGTH: 210
<212> TYPE: PRT
<213> ORGANISM: Homo sapiens

<400> SEQUENCE: 4

```
Met Ala Val Val Pro Leu Leu Leu Gly Gly Leu Trp Ser Ala Val
1               5                   10                  15

Gly Ala Ser Ser Leu Gly Val Val Thr Cys Gly Ser Val Val Lys Leu
            20                  25                  30

Leu Asn Thr Arg His Asn Val Arg Leu His Ser His Asp Val Arg Tyr
        35                  40                  45

Gly Ser Ser Ser Gly Gln Gln Ser Val Thr Gly Val Thr Ser Val Asp
```

```
            50                  55                  60
Asp Ser Asn Ser Tyr Trp Arg Ile Arg Arg Lys Ser Ala Thr Val Cys
 65                  70                  75                  80

Glu Arg Gly Thr Pro Ile Lys Cys Gly Gln Pro Ile Arg Leu Thr His
                 85                  90                  95

Val Asn Thr Gly Arg Asn Leu His Ser His His Phe Thr Ser Pro Leu
            100                 105                 110

Ser Gly Asn Gln Glu Val Thr Ala Phe Gly Glu Gly Glu Gly Asp
        115                 120                 125

Tyr Leu Asp Asp Trp Thr Val Leu Cys Asn Gly Pro Tyr Trp Val Arg
130                 135                 140

Asp Gly Glu Val Arg Phe Lys His Ser Ser Thr Glu Val Leu Leu Ser
145                 150                 155                 160

Val Thr Gly Glu Gln Tyr Gly Arg Pro Ile Ser Gly Gln Lys Glu Val
                165                 170                 175

His Gly Met Ala Gln Pro Ser Gln Asn Asn Tyr Trp Lys Ala Met Glu
            180                 185                 190

Gly Ile Phe Met Lys Pro Ser Glu Leu Leu Lys Ala Glu Ala His His
        195                 200                 205

Ala Glu
    210

<210> SEQ ID NO 5
<211> LENGTH: 60
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: 60
<223> OTHER INFORMATION: n = g, a, c or t.

<400> SEQUENCE: 5
gagagagaga ctcgagcggc cgcaaggatc ctaattagtt agtttttttt ttttttttvn    60

<210> SEQ ID NO 6
<211> LENGTH: 19
<212> TYPE: DNA
<213> ORGANISM: Artificial Sequence
<220> FEATURE:
<223> OTHER INFORMATION: Primer Sequence

<400> SEQUENCE: 6
ataggtccag gtcgtcgcc                                                  19

<210> SEQ ID NO 7
<211> LENGTH: 19
<212> TYPE: DNA
<213> ORGANISM: Artificial Sequence
<220> FEATURE:
<223> OTHER INFORMATION: Primer Sequence

<400> SEQUENCE: 7
tccgtatttg atgtcgtgc                                                  19

<210> SEQ ID NO 8
<211> LENGTH: 18
<212> TYPE: DNA
<213> ORGANISM: Artificial Sequence
<220> FEATURE:
<223> OTHER INFORMATION: Primer Sequence
```

```
<400> SEQUENCE: 8
ctgctggcgc tgttagtg                                            18

<210> SEQ ID NO 9
<211> LENGTH: 18
<212> TYPE: DNA
<213> ORGANISM: Artificial Sequence
<220> FEATURE:
<223> OTHER INFORMATION: Primer Sequence

<400> SEQUENCE: 9
gcgcactgtc cataggtc                                            18
```

MANNOSYLTRANSFERASE POLYPEPTIDES AND POLYNUCLEOTIDES ENCODING THEM AND METHODS FOR MAKING AND USING THEM

TECHNICAL FIELD

The present invention relates to a novel protein having signal sequence, which is derived from human fetal hepatocytes, genes encoding said protein, and a method for producing and using the same.

BACKGROUND ART

Based on their characteristics, proteins synthesized in cells can be categorized into the following groups of proteins: (1) those localized in various intracellular organelles, such as, the nucleus, mitochondria, and cytoplasm; (2) those functioning on the cell membrane, such as, receptors and channel molecules; and (3) those functioning after being secreted to the outside of cells, such as, growth factors and cytokines. Among others, secretory proteins specifically play biologically important roles in growth of cells, regulation of differentiation and apoptosis, inflammatory reactions, intercellular interaction, etc. Thus, the secretory proteins are the preferred target molecules of diagnostic and therapeutic drugs for various diseases.

Tissues at fetal stages, as compared to adult tissues wherein most of the cells are in a resting phase, express various genes and result in dynamic changes, such as, cell growth, regeneration, differentiation, and cell death. For example, fetal liver is an essential tissue for hemopoiesis and expresses various important genes participating in the maintenance of life. Thus, fetal liver is a preferred target to isolate genes playing important roles in living cells. Furthermore, molecules expressed at high levels in fetal liver are predicted to play important roles in living cells.

DISCLOSURE OF THE INVENTION

The present invention provides a novel protein having a signal sequence, which is derived from human fetal hepatocytes, genes encoding said protein, molecules functionally equivalent thereto, and methods for producing and using the same.

To achieve the above objectives, the present inventors screened a cDNA library synthesized from human fetal hepatocytes using the TMT (Transmembrane Trap) method, which was originally developed by the present inventors (International Publication WO 99/60113). They succeeded in isolating a cDNA encoding a novel protein having a signal sequence (the clone was dubbed "SMAP-1")

Expression of SMAP-1 mRNA in tissue was examined by RT-PCR (reverse transcriptase-polymerase chain reaction). The gene was found to be expressed in all tested tissues, i.e., brain, heart, liver, spleen, kidney, and lymphocyte. In particular, markedly high levels of expression was detected in the liver and kidney. Since SMAP-1 was expressed in fetal liver and all the tested (adult) tissues, this raises the possibility that it is an important molecule involved in the development and maintenance of living cells. Furthermore, since fetal liver is an important tissue for hemopoiesis at the fetal stage, SMAP-1 may be a regulatory factor for growth and differentiation of hemopoietic cells. SMAP-1 is suggested to be involved to fibrosis of liver and kidney, particularly, due to its strong expression in liver and kidney.

According to the results of database searching, SMAP-1 was shown to have homology with yeast mannosyltransferase. Therefore, SMAP-1 has been suggested to function as a glycosyltransferase. Recently, it was suggested that changes in sugar chains of glycoproteins expressed on cell surfaces are associated with metastasis and ingravescence of cancers. For example, the cell surface molecule Muc1 mucin that contains many O-linked sugar chains has been suggested to be involved in the ingravescence of colon cancer and kidney cancer to higher malignancy. Thus this molecule has been regarded a tumor marker. Therefore, abnormalities of SMAP-1 may result in aberrant intercellular recognition and interaction via an alteration of sugar chains of cancer antigens, and thus may be involved in infiltration and metastasis of cancer cells, angiogenesis, and so on. Furthermore, SMAP-1 expressed at normal levels may function to regulate mutual recognition and communication between immune cells, such as, lymphocytes, and leukocytes, and vascular epithelia. Thus, agents suppressing cancer metastasis and immuno-modifiers whose target is SMAP-1 may be developed.

On the other hand, changes of sugar chains of transmembrane proteins alter signals for growth, differentiation, and apoptosis of cells. For example, excessive addition of sugar chains to EGF (epidermal growth factor) receptor enhances the downstream signal and results in a marked enhancement of cell growth. These findings indicate that SMAP-1 may regulate growth, differentiation and apoptosis of cells by modulating sugar chains of transmembrane proteins. Thus, anti-cancer drugs and agents for regulating growth, differentiation, and apoptosis of cells may be developed using SMAP-1 as the target.

Increase of high mannose-type sugar chains and O-linked sugar chains on glycoproteins in brain in the course of aging suggests a relationship between glycosyltransferase and aging. Considering this fact that SMAP-1 is expressed in brain, abnormalities of SMAP-1 may also participate in brain senescence. Thus, therapeutic agents for Alzheimer's disease that target SMAP-1 may also be developed.

Furthermore, the promoter region of SMAP-1 was searched for binding motifs for various transcription factors and transcription regulatory factors. As a result, binding motifs for various transcription factors including AML-1 (acute myelogenous leukemia-1), GATA-1, GATA-2, GATA-3, AP-1 (activator protein-1), NF-κB (nuclear factor-kappa B), c-Ets, Pbx-1, SRY (sex determining region on the Y), Sox-5 (SRY box-5), and HSF (hepatocyte stimulating factor), were detected.

AML-1 is an important transcription factor that regulates the growth and differentiation of hemopoietic cells at early stages of hemopoiesis. The abnormality of AML-1 by chromosomal translocation is closely associated with the onset of leukemia. The presence of AML-1-binding motif in the promoter region of SMAP-1 suggests that SMAP-1 may be an important molecule functioning in the production of adult-type blood (the process of differentiation and proliferation of hematopoietic stem cells to all lineages of hemocytes in fetal liver). In addition, it also suggests that abnormalities of AML-1 may induce aberrant expression of SMAP-1 to cause the onset of acute leukemia. Thus, development of therapeutic agents for leukemia whose target is SMAP-1 may be considered.

Furthermore, the presence of binding motifs for GATA-1, GATA-2, and GATA-3 in the SMAP-1 promoter region suggests that SMAP-1 is associated with the regulation of growth, differentiation, and apoptosis of cells at each differentiation stage of hemopoiesis. GATA-1 is a transcription factor that plays an important role in the process of final differentiation from proerythroblast to mature erythrocyte, formation of platelet from megakaryocyte, and formation of connective tissue mast cells; which suggests that SMAP-1 regulates the proliferation, differentiation, and apoptosis of erythrocytes, megakaryocytes, and connective tissue mast cells. GATA-2 is a transcription factor that plays an important role in the maintenance and proliferation of hematopoietic stem cells, differentiation of mast cells, and development of urinary system; which suggests that SMAP-1 is a molecule functioning in the maintenance and proliferation of hematopoietic stem cells, differentiation of mast cells, and development of urinary system. GATA-3 is an essential transcription factor for differentiation of T cells and formation of Th2 cells; which suggests SMAP-1 to be a molecule functioning in T cell differentiation and differentiation of CD4+ T cells to Th2 cell (enhancement of differentiation to Th2 cells or suppression of differentiation to Th1 cells). As described above, the presence of GATA-1, GATA-2, and GATA-3 binding motifs in SMAP-1 suggests the possibility of developing drugs enhancing the growth of hematopoietic stem cell and hemocytes of each lineage, anti-allergy agents, and immuno-modifiers by targeting SMAP-1.

AP-1 and NF-κB are transcription factors that induce the production of inflammatory cytokines, such as IL-1, TNF, and IL-6. The presence of the binding motifs for these transcription factors in the SMAP-1 promoter region suggests the possibility that SMAP-1 is an inflammatory cytokine whose expression is enhanced by AP-1 and NF-κB at the time of inflammation. Thus, anti-inflammatory drugs whose target is SMAP-1 may be developed.

c-Ets and Pbx-1 are transcription factors that are expressed in lymphocytes. Therefore, SMAP-1 is suggested to regulate proliferation, differentiation, and apoptosis of lymphocytes. Thus, it may be possible to develop immuno-modifiers that target SMAP-1.

SRY and Sox-5 are transcription factors involved in spermatogenesis, which suggests the possibility of SMAP-1 to function in the processes of differentiation and maturation of sperm.

The presence of HSF (heat shock factor)-binding motifs in the SMAP-1 promoter region suggests SMAP-1 to exhibit the activity of protecting the cells from the stress when cells are exposed to some stress, such as physical, hypoxic, heat, and UV. Specifically, enhanced expression of SMAP-1 due to HSF may play an important role in the survival of cells by suppressing necrosis and apoptosis of cells. Thus, the possibility to develop drugs for myocardial infarction, brain infarction, and ischemic reperfusion injury that target SMAP-1 is suggested.

As described above, SMAP-1 is assumed to play important roles in living cells, and is particularly useful as a target of drug development.

The present invention relates to a novel protein "SMAP-1" having a signal sequence, which is derived from human fetal hepatocyte, genes encoding said protein, molecules functionally equivalent thereto, and a method for producing and using the same. More specifically, the present invention provides:

[1] a DNA selected from the group consisting of:
(a) a DNA encoding a protein comprising the amino acid sequence of SEQ ID NO: 2;
(b) a DNA containing the coding region of the nucleotide sequence of SEQ ID NO: 1;
(c) a DNA encoding a protein functionally equivalent to the protein consisting of the amino acid sequence of SEQ ID NO: 2, which comprises the amino acid sequence of SEQ ID NO: 2, wherein one or more amino acids have been substituted, deleted, inserted, and/or added; and
(d) a DNA encoding a protein functionally equivalent to the protein consisting of the amino acid sequence of SEQ ID NO: 2, that hybridizes under a stringent condition to a DNA consisting of the nucleotide sequence of SEQ ID NO: 1;

[2] a DNA encoding a partial peptide of the protein consisting of the amino acid sequence of SEQ ID NO: 2;

[3] a protein or a peptide encoded by the DNA of [1] or [2];

[4] a vector wherein the DNA of [1] or [2] has been inserted;

[5] a host cell containing the DNA of [1] or [2], or the vector of [4];

[6] a method for producing the protein or peptide of [3], wherein said method comprises the steps of: (1) culturing the host cell of [5]; and (2) recovering the expressed protein from the host cell or the culture supernatant thereof;

[7] an antibody binding to the protein of [3];

[8] a polynucleotide containing at least 15 nucleotides that are complementary to a DNA consisting of the nucleotide sequence of SEQ ID NO: 1 or the complementary strand thereof; and

[9] a method of screening for a compound binding to the protein of [3]; which comprises the steps of:
(a) contacting a test sample with the protein or a partial peptide thereof;
(b) detecting the binding activity of the test sample to the protein or a partial peptide thereof; and
(c) selecting the compound that has the activity of binding to the protein or a partial peptide thereof.

The present invention provides a gene "SMAP-1" which encodes a novel protein that has a signal sequence. The nucleotide sequence of human SMAP-1 cDNA is shown in SEQ ID NO: 1, and the amino acid sequence of the protein encoded by the cDNA is shown in SEQ ID NO: 2. As shown in SEQ ID NO: 1, the human SMAP-1 cDNA has an ORF (open reading frame) encoding a protein consisting of 221 amino acids.

The SMAP-1 protein of the present invention is a molecule isolated by the TMT method. The existence of a potential transmembrane domain or signal sequence was predicted in the N-terminal region thereof with analysis software SOSUI. Further, the N-terminal region was predicted to be a signal sequence by the analysis using PSORT, which is a computer program for speculating the localization of proteins in cells. These results suggest that SMAP-1 protein functions as a secretory protein containing a signal sequence at the N-terminus. As described above, based on the expression pattern and structural properties, SMAP-1 is predicted to be a molecule playing an important role in living cells, and thus may be useful as a target for drug development.

Another aspect of the present invention encompasses proteins functionally equivalent to the human SMAP-1 protein (SEQ ID NO: 2). Such proteins include, for example, mutants of human SMAP-1 protein, non-human homologues of the protein, and so on. As used herein, "functionally equivalent" means that the protein of interest is similar to SMAP-1 protein and functions as a protein having a signal sequence. Such a function includes, for example, a function described in International publication WO 00/00610 and functions as a secretory protein. Whether an object protein is a secretory protein or not can be determined according to the following method.

First, a human SMAP-1 fusion gene is prepared by ligating a gene, which encodes a commercially available peptide (for example, His-tag or FLAG), to the 3'-end of the human SMAP-1 gene. Then, the fusion gene is introduced into animal cells (for example, COS cell, etc.) with an expression vector for animal cells (for example, pcDNA3, pCOS-1, etc.). Then human SMAP-1 is expressed as a fusion protein comprising the peptide. Whether the human SMAP-1 fusion protein is secreted into the culture supernatant or not is evaluated by ELISA, Western blotting, or immunoprecipitation using antibodies against the peptide.

Secretory proteins have various industrial advantages. For example, when preparation of recombinant proteins is desired, the proteins can be expressed in cells as fusion proteins fused with a secretory protein or a partial peptide thereof that is responsible for secretion. Thus, the fusion protein is secreted to the outside of the cells, which is advantageous for readily purifying the recombinant protein. In addition, many types of secretory proteins have been used as useful pharmaceuticals. Thus the protein of the present invention itself may be applicable as a pharmaceutical.

One method well known to those skilled in the art for preparing functionally equivalent proteins is to introduce mutations into proteins. For example, one skilled in the art can prepare proteins functionally equivalent to human SMAP-1 protein by introducing appropriate mutations into the amino acid sequence of the protein (SEQ ID NO: 2), by site-specific mutagenesis (Hashimoto-Gotoh, T. et al. (1995) Gene 152, 271–275; Zoller, M J, and Smith, M. (1983) Methods Enzymol. 100, 468–500; Kramer, W. et al. (1984) Nucleic Acids Res. 12, 9441–9456; Kramer W, and Fritz H J (1987) Methods. Enzymol. 154, 350–367; Kunkel, T A (1985) Proc Natl Acad Sci U S A. 82, 488–492; Kunkel (1988) Methods Enzymol. 85, 2763–2766), and so on. Mutation of amino acids may occur in nature too. Furthermore, the proteins of the present invention include a protein comprising the amino acid sequence of human SMAP-1 protein (SEQ ID NO: 2) in which one or more amino acids have been mutated, wherein the protein is functionally equivalent to SMAP-1 protein. In such a mutant protein, the number of amino acids mutated are considered to be usually 50 residues or less, preferably 30 residues or less, more preferably 10 residues or less (for example, 5 residues or less).

It is preferable to mutate an amino acid residue into one that allows the properties of the amino acid side-chain to be conserved. Examples of properties of amino acid side chains include: hydrophobic amino acids (A, I, L, M, F, P, W, Y, V), hydrophilic amino acids (R, D, N, C, E, Q, G, H, K, S, T), and amino acids comprising the following side chains: aliphatic side-chains (G, A, V, L, I, P); hydroxyl group-containing side-chains (S, T, Y); sulfur atom-containing side-chains (C, M); carboxylic acid- and amide-containing side-chains (D, N, E, Q); base-containing side-chain (R, K, H); and aromatic-containing side-chains (H, F, Y, W) (The letters within parenthesis indicate the one-letter codes of amino acids).

It is well known that a protein modified by deletion, addition, and/or substitution of one or more amino acid residues in the sequence of the protein can retain the original biological activity (Mark D. F. et al., Proc. Natl. Acad. Sci. U.S.A. 81: 5662–5666 (1984); Zoller M. J. and Smith M., Nucleic Acids Res. 10: 6487–6500 (1982); Wang A. et al., Science 224: 1431–1433; Dalbadie-McFarland G. et al., Proc. Natl. Acad. Sci. U.S.A. 79: 6409–6413 (1982)).

A protein in which amino acid residues have been added to the amino acid sequence of human SMAP-1 protein includes a fusion protein comprising the human SMAP-1 protein. The present invention includes a fusion protein in which human SMAP-1 protein and one or more of other proteins or peptides are fused. Methods well known in the art may be used to generate a fusion protein of the present invention. For example, a DNA encoding human SMAP-1 protein (SEQ ID NO: 2) and a DNA encoding another protein or peptide are linked in frame and introduced into an expression vector. The fusion protein is then expressed in a host cell. The protein or peptide fused to a protein of the present invention is not limited to any specific protein or peptide.

Known peptides, for example, FLAG (Hopp, T. P. et al., Biotechnology (1988) 6, 1204–1210), 6×His containing six His (histidine) residues, 10×His, Influenza agglutinin (HA), human c-myc fragment, VSP-GP fragment, p18HIV fragment, T7-tag, HSV-tag, E-tag, SV40T antigen fragment, lck tag, α-tubulin fragment, B-tag, Protein C fragment, etc., can be used as peptides that are fused to a protein of the present invention. Examples of proteins that are fused to a protein of the invention are, GST (glutathione-S-transferase), Influenza agglutinin (HA), immunoglobulin constant region, β-galactosidase, MBP (maltose-binding protein), etc. Fusion proteins can be prepared by fusing commercially available DNA encoding these peptides or proteins with a DNA encoding the protein of the present invention and expressing the fused DNA thus prepared.

An alternative method known to those skilled in the art for preparing functionally equivalent proteins is the method utilizing the hybridization technique (Sambrook, J. et al., Molecular Cloning 2nd ed. 9.47–9.58, Cold Spring Harbor Lab. Press, 1989). Generally, one skilled in the art can isolate DNAs highly homologous to the whole or part of a DNA sequence encoding the human SMAP-1 protein (SEQ ID NO: 1), and then isolate a protein functionally equivalent to the human SMAP-1 protein from those DNA thus isolated. The present invention includes proteins that are functionally equivalent to the human SMAP-1 protein, those proteins that are encoded by DNAs hybridizing to a DNA encoding the human SMAP-1 protein. Such proteins include homologues derived from human and non-human mammalians (for example, proteins encoded by mouse, rat, rabbit, cattle, etc.).

Suitable hybridization conditions for isolating DNAs encoding proteins functionally equivalent to human SMAP-1 protein can be selected by those skilled in the art. Such a hybridization condition includes, for example, a condition with low stringency. An exemplary condition with low stringency includes post-hybridization wash in 2× SSC and 0.1% SDS at 42° C., preferably in 2× SSC and 0.1% SDS at 50° C. More preferred hybridization conditions include those realizing high stringency. The condition of high stringency includes, for example, washing in 0.1× SSC and 0.1% SDS at 65° C. According to these conditions, the higher the temperature, a DNA with higher homology will be efficiently obtained. However, several factors including temperature and salt concentration can influence the stringency of hybridization and one skilled in the art can suitably select the factors to accomplish a similar stringency.

In place of hybridization, a gene amplification method using primers that have been synthesized based on sequence information of the DNA (SEQ ID NO: 1) encoding the human SMAP-1 protein via the polymerase chain reaction (PCR) method can also be utilized.

A protein functionally equivalent to human SMAP-1 protein encoded by a DNA isolated through the above hybridization technique or via gene amplification techniques normally has a high homology to the amino acid sequence of human SMAP-1 protein (SEQ ID NO: 2). The proteins of the present invention also include proteins that are functionally equivalent to human SMAP-1 protein and are highly homologous to the amino acid sequence shown in SEQ ID NO: 2. "Highly homologous" refers to normally an identity, at the amino acid level, of at least 65% or higher, preferably 75% or higher, more preferably 85% or higher, and most preferably 95% or higher. The homology of a protein can be determined by following the algorithm of Wilbur and Lipman (Wilbur, W. J. and Lipman, D. J. (1983) Proc. Natl. Acad. Sci. USA 80: 726–730).

Depending on the cell or host used to produce it or the purification method utilized (described below), the proteins of the present invention may have variations in their amino acid sequence, molecular weight, isoelectric point, the presence or absence of sugar chains, form, etc. Nevertheless, as long as the obtained protein has a function equivalent to human SMAP-1 protein, it is within the scope of the present invention. For example, if a protein of the present invention is expressed in a prokaryotic cell, such as E. coli, the protein includes a methionine residue at the N-terminus in addition to the natural amino acid sequence of the protein. Such proteins are also included within the proteins of the present invention.

The proteins of the present invention can be prepared as recombinant proteins or as naturally occurring proteins, using methods commonly known in the art. When the protein is a recombinant protein, it may be produced by inserting a DNA (for example, a DNA having the nucleotide sequence of SEQ ID NO: 1) encoding a protein of the present invention into an appropriate expression vector, collecting the transformant obtained after introducing the vector into an appropriate host cell, obtaining an extract, and then purifying and preparing the protein using ion exchange, reverse phase, gel filtration, or affinity chromatography. Affinity chromatography may be done using a column in which an antibody against a protein of the present invention is fixed. A combination of such columns may also be used.

Alternatively, when a protein of the invention is expressed in host cells (e.g., animal cells or E. coli) as a fusion protein with glutathione S transferase protein, or a recombinant protein with multiple histidine residues, the expressed recombinant protein can be purified using a glutathione column or nickel column. After the fusion protein is purified, if necessary, regions of the fusion protein (apart from the desired protein) can be digested and removed with thrombin, factor Xa, etc.

A native protein of the invention can be isolated by methods well known in the art. For example, affinity column to which an antibody binding to the protein of the present invention is bound can be employed to purify an extract of tissues or cells that express the protein of the present invention (described below). The antibody may be a polyclonal or monoclonal antibody.

The present invention also includes partial peptides of the proteins of the present invention. The partial peptides of the present invention comprise at least 7 or more amino acids, preferably 8 or more amino acids, and more preferably 9 or more amino acids. The partial peptides can be used, for example, for generating antibodies against a protein of the present invention, screening of compounds binding to a protein of the present invention, or screening of stimulators or inhibitors of a protein of the present invention. Additionally, they may be antagonists or competitive inhibitors of the proteins of the present invention. The partial peptides of the present invention can be produced by genetic engineering methods, known peptide synthesis methods, or by cutting the proteins of the present invention by appropriate peptidases. Synthesis of the peptides may be conducted according to, for example, the solid phase synthesis method or the liquid phase synthesis method.

In addition to the use of a DNA encoding a protein of the present invention in the above-described in vivo or in vitro production of a protein of the present invention, the DNA encoding a protein of the present invention may also be applied, for example, in the gene therapy of diseases caused by an aberration in a gene encoding a protein of the present invention or diseases treatable by a protein of the present invention. Any type of DNA, such as cDNA synthesized from mRNA, genomic DNA, or synthetic DNA can be used so long as the DNA encodes a protein of the present invention. Also so long as they can encode a protein of the present invention, DNA comprising arbitrary sequences based on the degeneracy of the genetic code are also included.

The DNA of the present invention can be prepared by methods known in the art. For example, a cDNA library can be constructed from cells expressing a protein of the present invention and hybridization can be conducted using a part of the DNA sequence of the present invention (for example, SEQ ID NO: 1) as a probe. The cDNA library may be prepared, for example, according to the method described in the literature (Sambrook J. et al. Molecular Cloning, Cold Spring Harbor Laboratory Press (1989)), or instead, commercially available cDNA libraries may be used. Alternatively, a DNA of the present invention can be obtained by preparing RNA from cells expressing a protein of the present invention, synthesizing cDNA by a reverse transcriptase, synthesizing oligo-DNA based on a DNA sequence of the present invention (for example, SEQ ID NO: 1), and amplifying the cDNA encoding a protein of the present invention by PCR using the oligo-DNA as primers.

The nucleotide sequence of the obtained cDNA is determined to find an open reading frame, and thereby, the amino acid sequence of a protein of the invention can be obtained. The cDNA obtained may also be used as a probe for screening a genomic library to isolate genomic DNA.

More specifically, mRNA may first be isolated from cell, tissue, or organ in which a protein of the invention is expressed (e.g. tissues such as brain, skeletal muscle, testis, placenta, large intestine, spleen, and cartilage). Known methods can be used to isolate mRNA; for instance, total RNA is prepared by guanidine ultracentrifugation (Chirgwin J. M. et al. Biochemistry 18:5294–5299 (1979)) or AGPC method (Chomczynski P. and Sacchi N. Anal. Biochem. 162:156–159 (1987)), and mRNA is purified from total RNA using mRNA Purification Kit (Pharmacia) and such. Alternatively, mRNA may be directly prepared by QuickPrep mRNA Purification Kit (Pharmacia).

The obtained mRNA is used to synthesize cDNA using reverse transcriptase. cDNA may be synthesized using a kit such as the AMV Reverse Transcriptase First-strand cDNA Synthesis Kit (Seikagaku Kogyo). Alternatively, cDNA may be synthesized and amplified following the 5'-RACE method (Frohman M. A. et al., Proc. Natl. Acad. Sci. U.S.A. 85: 8998–9002 (1988); Belyavsky A. et al., Nucleic Acids Res. 17: 2919–2932 (1989)) that uses primers and such described herein, the 5'-Ampli FINDER RACE Kit (Clontech), and polymerase chain reaction (PCR).

A desired DNA fragment is prepared from the PCR products and linked to a vector DNA. The recombinant vector is used to transform E. coli and such, and the desired recombinant vector is prepared from a selected colony. The nucleotide sequence of the desired DNA can be verified by conventional methods, such as dideoxynucleotide chain termination.

A DNA of the invention may be designed to have a sequence that is expressed more efficiently by taking into account the frequency of codon usage in the host used for expression (Grantham R. et al., Nucleic Acids Res. 9: 43–74 (1981)). The DNA of the present invention may be altered by a commercially available kit or a conventional method. For instance, the DNA may be altered by digestion with restriction enzymes, insertion of a synthetic oligonucleotide or an appropriate DNA fragment, addition of a linker, or insertion of the initiation codon (ATG) and/or the stop codon (TAA, TGA, or TAG), etc.

Specifically, the DNAs of the present invention include a DNA having the following nucleotide sequences: from A at position 27 to C at position 689 of SEQ ID NO: 1.

Furthermore, the DNAs of the present invention include a DNA hybridizing with a DNA having the nucleotide sequence of SEQ ID NO: 1, and encoding a protein functionally equivalent to a protein of the invention described above. Conditions for hybridization may be appropriately chosen by those skilled in the art. Specifically, conditions described above may be used. Under the conditions, DNA having higher homologies can be obtained by increasing the temperature. The above hybridizing DNA is preferably a natural DNA, for example, a cDNA or a chromosomal DNA.

The present invention also provides a vector into which a DNA of the present invention is inserted. The vectors of the present invention are useful in maintaining the DNA of the present invention within host cells, or expressing a protein of the present invention.

When E. coli is used as the host cell, there is no limitation other than that the vector should have an "ori", to amplify and mass-produce the vector in E. coli (e.g., JM109, DH5α, HB101, or XL1Blue), and such, and a marker gene for selecting the transformed E. coli (e.g., a drug-resistance gene selected by a drug (e.g., ampicillin, tetracycline, kanamycin, or chloramphenicol)). For example, M13-series vectors, pUC-series vectors, pBR322, pBluescript, pCR-Script, and such can be used. Besides the vectors, pGEM-T, pDIRECT, pT7, and so on can be also used for subcloning and excision of the cDNA as well. When a vector is used to produce a protein of the present invention, an expression vector is especially useful. When the expression vector is expressed, for example, in E. coli, it should have the above characteristics in order to be amplified in E. coli. Additionally, when E. coli, such as JM109, DH5α, HB101, or XL1-Blue, are used as the host cell, the vector should have a promoter, e.g. lacZ promoter (Ward et al. (1989) Nature 341:544–546; (1992) FASEB J. 6:2422–2427), araB promoter (Better et al. (1988) Science 240:1041–1043), or T7 promoter, that can efficiently promote the expression of the desired gene in E. coli. Other examples of the vectors include pGEX-5X-1 (Pharmacia), "QIAexpress system" (QIAGEN), pEGFP, and pET (for this vector, BL21, a strain expressing T7 RNA polymerase, is preferably used as the host).

Furthermore, the vector may comprise a signal sequence to secrete the polypeptide. For producing a protein into the periplasm of E. coli, the pelB signal sequence (Lei S. P. et al. J. Bacteriol. 169:4379 (1987)) may be used as the signal sequence for protein secretion. The calcium chloride method or electroporation may be used to introduce the vector into host cells.

As vectors used to produce the proteins of the present invention, expression vectors derived from mammals (e.g., pCDNA3 (Invitrogen), pEGF-BOS (Nucleic Acids Res. (1990) 18 (17): 5322), pEF, pCDM8); insect cells (e.g., "Bac-to-BAC baculovirus expression system" (GIBCO-BRL), pBacPAK8); plants (e.g. pMH1, pMH2); animal viruses (e.g., pHSV, pMV, pAdexLcw); retroviruses (e.g. pZIPneo); yeasts (e.g., "Pichia Expression Kit" (Invitrogen), pNV11, SP-Q01); and Bacillus subtilis (e.g. pPL608, pKTH50) may be employed besides E. coli.

In order to express proteins in animal cells, such as, CHO, COS, and NIH3T3 cells, the vector must have a promoter necessary for expression in such cells (e.g., SV40 promoter (Mulligan et al. (1979) Nature 277: 108), MMLV-LTR promoter, EF1α promoter (Mizushima et al. (1990) Nucleic Acids Res. 18: 5322), CMV promoter, etc.). It is preferable if the vector additionally has a marker gene for selecting transformants (for example, a drug resistance gene selected by a drug like neomycin, G418, etc.). Examples of vectors with such characteristics include pMAM, pDR2, pBK-RSV, pBK-CMV, pOPRSV, pOP13, and so on.

Furthermore, in order to stably express the gene and to amplify the copy number in cells, the method using CHO cells deficient in nucleic acid synthetic pathways as the host, incorporating into the CHO cells a vector (such as pCHOI) having a DHFR gene that compensates for the deficiency, and amplifying the vector with methotrexate (MTX) can be used. Alternatively, for transiently expressing a gene, the method that transforms COS cells that have the gene for SV40 T antigen on the chromosome with a vector (such as pcD) having the SV40 replication origin can be mentioned. The replication origin may be that of a polyomavirus, adenovirus, bovine papilloma virus (BPV), and the like. Also, to amplify the gene copy number in the host cells, selection markers, such as, the aminoglycoside transferase (APH) gene, thymidine kinase (TK) gene, E. coli xanthine-guanine phosphoribosyl transferase (Ecogpt) gene, and the dihydrofolate reductase (dhfr) gene may be comprised in the expression vector.

A DNA of the present invention can be expressed in animals by, for example, inserting a DNA of the invention into an appropriate vector and introducing this vector into a living cells via the retroviral method, the liposome method, the cationic liposome method, the adenovirus method, etc. Thus, it is possible to perform gene therapy of diseases caused by a mutation of the SMAP-1 gene of the present invention. The vectors used in these methods include, but are not limited to, adenovirus vectors (e.g., pAdexlcw), retrovirus vectors (e.g. pZIPneo), and so on. General techniques for gene manipulation, such as insertion of a DNA of the invention into a vector, can be performed according to conventional methods (Molecular Cloning, 5.61–5.63) Administration to living cells may be performed according the ex vivo method or according to the in vivo method.

The present invention also provides a host cell into which a vector of the present invention has been introduced. The host cell into which the vector of the invention is introduced is not particularly limited. For example, E. coli, various animal cells, and such, can be used. The host cell of the present invention can be used, for example, as a production system to produce and express a protein of the present invention. Protein production systems include in vitro and in vivo systems. Such production systems using eukaryotic cells or prokaryotic cells can be given as in vitro production systems.

Eukaryotic host cells, for example, animal cells, plant cells, and fungi cells can be used. Mammalian cells, for example, CHO (J.Exp.Med. (1995) 108:945), COS, 3T3, myeloma, BHK (baby hamster kidney), HeLa, Vero, amphibian cells (e.g., Xenopus oocytes (Valle et al. (1981) Nature 291:358–340), and insect cells (e.g. Sf9, Sf21, Tn5) are known as animal cells. Among CHO cells, those deficient in the DHFR gene, dhfr-CHO (Proc.Natl.Acad..Sci.USA (1980) 77:4216–4220) and CHO K-1 (Proc.Natl.Acad.Sci.USA (1968) 60:1275), are particularly preferable. Among animal cells, CHO cells are particularly preferable for large scale expression. A vector can be introduced into a host cell by, for example, the calcium phosphate method, the DEAE-dextran method, methods using cationic liposome DOTAP (Boehringer-Mannheim), electroporation, lipofection, etc. Plant cells originating from *Nicotiana tabacum* are known as protein producing systems and may be used as callus cultures. As fungal cells, yeast cells such as *Saccharomyces*, including *Saccharomyces cerevisiae*, or filamentous fungi such as *Aspergillus*, including *Aspergillus niger*, are known and are within the scope of this invention. Useful prokaryotic cells include bacterial cells. Bacterial cells (e.g., *E. coli*), JM109, DH5α, HB101, as well as *Bacillus subtilis* are known.

A desired DNA transforms these cells, and the resulting transformants are cultured in vitro to obtain a protein. Transformants can be cultured using known methods. For example, culture medium, such as DMEM, MEM, RPMI1640, or IMDM, may be used with or without serum supplements, such as fetal calf serum (FCS), as culture medium for animal cells. The pH of the culture medium is preferably between about 6 and 8. Such cells are typically cultured at about 30 to 40° C. for about 15 to 200 hr, and the culture medium may be replaced, aerated, or stirred if necessary.

Animal and plant hosts may be used for in vivo production. For example, a desired DNA can be introduced into an animal or plant host. Encoded proteins are produced in vivo, and then recovered. These animal and plant hosts are included in the "host" of the present invention.

Animals to be used for the production system described above include mammals and insects. Mammals such as goats, pigs, sheep, mice, and cattle may be used (Vicki Glaser, SPECTRUM Biotechnology Applications (1993)). Alternatively, the mammals may be transgenic animals.

For instance, a desired DNA may be prepared as a fusion gene with a gene, such as goat β casein gene, that encodes a protein specifically produced into milk. DNA fragments comprising the fusion gene are injected into goat embryos, which are then introduced back to female goats. Proteins are recovered from milk produced by the transgenic goats (i.e., those born from the goats that had received the modified embryos) or from their offspring. To increase the amount of milk containing the proteins produced by transgenic goats, appropriate hormones may be administered (Ebert K. M. et al. (1994) Bio/Technology 12: 699–702).

Alternatively, insects, such as silkworm, may be used as the host. Baculoviruses, into which a DNA encoding a desired protein has been inserted, can be used to infect silkworms, and the desired protein recovered from body fluids (Susumu M. et al. (1985) Nature 315: 592–594).

As plants, tobacco can be used. When using tobacco, a DNA encoding a desired protein may be inserted into a plant expression vector, such as pMON 530, which is introduced into bacteria, such as *Agrobacterium tumefaciens*. Then, the bacteria are used to infect tobacco, such as *Nicotiana tabacum*, and the desired polypeptide is recovered from the leaves (Julian K. -C. Ma et al. (1994) Eur. J. Immunol. 24: 131–138).

A protein of the present invention obtained as above may be isolated from inside or outside of hosts (medium, etc.), and purified as a substantially pure homogeneous protein. The method for protein isolation and purification is not limited to any specific method; in fact, any standard method may be used. For instance, column chromatography, filters, ultrafiltration, salting out, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the protein.

Chromatography, such as, affinity chromatography, ion-exchange chromatography, hydrophobic chromatography, gel filtration chromatography, reverse phase chromatography, adsorption chromatography, etc. maybe used (Strategies for Protein Purification and Characterization: A Laboratory Course Manual. Ed. Daniel R. Marshak et al., Cold Spring Harbor Laboratory Press (1996)). These chromatographies may be performed by liquid chromatographies, such as HPLC and FPLC. Thus, the present invention provides highly purified proteins produced by the above methods.

A protein may be optionally modified or partially deleted by treating it with an appropriate protein-modifying enzyme before or after purification. For example, trypsin, chymotrypsin, lysylendopeptidase, protein kinase, glucosidase, and such are used as protein-modifying enzymes.

The present invention also provides antibodies binding to a protein of the present invention. The antibodies of the present invention may take any form, including monoclonal antibodies and polyclonal antibodies. Furthermore, antiserum obtained by immunizing animals such as rabbits, with a protein of the instant invention, all classes of polyclonal and monoclonal antibodies, as well as human and humanized antibodies produced by genetic recombination are within the scope of the present invention.

A protein of the invention used as a sensitizing antigen to obtain antibodies may be derived from any animal species. However, it is preferably from a mammal like human, mouse, or rat (more preferably from a human). A human-derived protein may be obtained using a nucleotide or amino acid sequence disclosed herein.

A full-length protein or a partial peptide thereof may be used as a sensitizing antigen in the present invention. A partial peptide may be, for example, an amino (N)-terminus or carboxy (C)-terminus fragment of the protein. Herein, an "antibody" is defined as an antibody that reacts with either the full length or a fragment of the protein.

A gene encoding a protein of the invention or its fragment may be inserted into a known expression vector used to transform a host cell as described herein. The desired protein or its fragment may be recovered from the outside or inside of host cells by any standard methods, and may be used as the sensitizing antigen. Alternatively, cells expressing the protein or their lysates, or a chemically synthesized protein may be used as an antigen. Preferably, short peptides are used as antigens by appropriately binding to carrier proteins, such as keyhole limpet hemocyanin, bovine serum albumin, and ovalbumin.

Any mammal may be immunized with the sensitizing antigen. However, preferably, the compatibility with parental cells used for cell fusion is taken into account. In general, animals of Rodentia, Lagomorpha or Primates are used.

Animals of Rodentia include, for example, mice, rats, and hamsters. Animals of Lagomorpha include, for example, rabbits. Animals of Primates include, for example, monkeys of Catarrhini (old world monkeys), such as *Macaca fascicularis*, rhesus monkeys, sacred baboons, or chimpanzees.

Methods for immunizing animals with antigens are well known in the art. Intraperitoneal injection or subcutaneous injection of antigens is used as a standard method. More specifically, antigens may be diluted and suspended in an appropriate amount with phosphate buffered saline (PBS), physiological saline, etc. If desired, the antigen suspension may be mixed with an appropriate amount of a standard adjuvant, such as Freund's complete adjuvant, made into an emulsion, and then administered to mammals. Preferably, this is followed by several administrations of the antigen mixed with an appropriate amount of Freund's incomplete adjuvant every 4 to 21 days. An appropriate carrier may also be used for immunization. After the above immunization, the serum is examined for an increase of the amount of desired antibodies by a standard method.

Polyclonal antibodies raised against a protein of the present invention may be prepared by collecting blood from the immunized mammal after confirming the increase of desired antibodies in the serum, and by separating serum from the blood by any conventional method. Serum containing a polyclonal antibody may also be used as a polyclonal antibody, or if necessary, the fraction containing the polyclonal antibody may be isolated from the serum. For example, fractions that recognize only a protein of the present invention are obtained using affinity columns to which the present protein is coupled, followed by purifying the fraction using a protein A or G column to prepare immunoglobulin G or M.

To prepare monoclonal antibodies, immune cells are collected from a mammal immunized with an antigen and checked for an increase of the level of the desired antibodies in the serum as described above, and these cells are subjected to cell fusion. The immune cells used for cell fusion are preferably obtained from the spleen. The other parent cell fused with the above immune cell is preferably a mammalian myeloma cell, and more preferably, a myeloma cell that has acquired a special feature that can be used for selecting fusion cells by a drug.

The above immune cell and myeloma cell may be fused by basically any standard method, such as those described in literature (Galfre G. and Milstein C. Methods Enzymol. 73: 3–46 (1981)).

Resulting hybridomas obtained by the cell fusion may be selected by cultivating them in a standard selection medium, such as the HAT medium (hypoxanthine, aminopterin, and thymidine containing medium). The cell culture is typically continued in the HAT medium for a period of time that is sufficient to allow all cells except the desired hybridoma (non-fused cells) to die, usually from several days to several weeks. Then, standard limiting dilution is performed to screen and clone a hybridoma cell producing the desired antibody.

Besides the above method in which a nonhuman animal is immunized with an antigen for preparing a hybridoma, human lymphocytes such as those infected by the EB virus may be immunized with a protein, protein-expressing cells, or their lysates in vitro. Then, the immunized lymphocytes are fused with human-derived myeloma cells with indefinite division ability, such as U266; to yield a hybridoma producing a desired human antibody binding to a protein of the invention (JP-A No. Sho 63-17688).

Subsequently, the hybridomas thus obtained are transplanted into the abdominal cavity of a mouse from which the ascites is collected. The monoclonal antibodies thus obtained can be purified by, for example, ammonium sulfate precipitation or column chromatography using a protein A or protein G column, a DEAE ion exchange column, an affinity column to which a protein of the invention is coupled, and such. An antibody of the invention can be used not only for purifying and detecting a protein of the invention, but also as a candidate for an agonist or antagonist of a protein of the present invention. Such an antibody is also expected to be used for antibody therapy of diseases in which the proteins of this invention are involved. To administer the obtained antibody to human bodies (namely, antibody therapy), human antibodies or humanized antibodies are preferred to reduce immunogenicity.

For example, transgenic animals having a repertory of human antibody genes may be immunized with a protein, protein expressing cells, or their lysates as antigen. Antibody producing cells are collected from the animals, and fused with myeloma cells to obtain hybridoma, from which human antibodies against the protein can be prepared (see WO92-03918, WO93-2227, WO94-02602, WO94-25585, WO96-33735, and WO96-34096).

Alternatively, an immune cell that produces antibodies, such as an immunized lymphocyte, may be immortalized by an oncogene and used for preparing monoclonal antibodies.

Such monoclonal antibodies can also be recombinantly prepared using genetic engineering techniques (see, for example, Borrebaeck C. A. K. and Larrick J. W., Therapeutic Monoclonal Antibodies, published in the United Kingdom by MacMillan Publishers LTD (1990)). A recombinant antibody can be prepared by cloning a DNA encoding the antibody from an immune cell, such as a hybridoma or an immunized lymphocyte producing the antibody; inserting this into an appropriate vector; and introducing the vector into a host cell. The present invention also encompasses recombinant antibodies prepared as described above.

An antibody of the present invention may be a fragment of an antibody or modified antibody as long as it binds to one or more of the proteins of the invention. For instance, the antibody fragment may be Fab, F (ab')$_2$, Fv, or single chain Fv (scFv) in which Fv fragments from H and L chains are linked by an appropriate linker (Huston J. S. et al. (1988) Proc. Natl. Acad. Sci. U.S.A. 85:5879–5883). More specifically, treating an antibody with an enzyme such as papain or pepsin may generate an antibody fragment. Alternatively, a gene encoding the antibody fragment may be constructed, inserted into an expression vector, and expressed in an appropriate host cell (see, for example, Co M. S. et al. (1994) J. Immunol. 152:2968–2976; Better M. and Horwitz A. H. (1989) Methods Enzymol. 178: 476–496; Pluckthun A. and Skerra A. (1989) Methods Enzymol. 178: 497–515; Lamoyi E. Methods Enzymol. (1986) 121: 652–663; Rousseaux J. et al. (1986) Methods Enzymol. 121: 663–669; Bird R. E. and Walker B. W. (1991) Trends Biotechnol. 9: 132–137).

An antibody may be modified by conjugation with a variety of molecules, including polyethylene glycol (PEG). The present invention provides such modified antibodies. A modified antibody can be obtained by chemically modifying an antibody. These modification methods are conventional in the field.

Alternatively, an antibody of the present invention may be obtained as a chimeric antibody comprising a variable region derived from a nonhuman antibody and the constant region derived from a human antibody, or as a humanized antibody comprising the complementarity determining region (CDR) derived from a nonhuman antibody, the framework region (FR) derived from a human antibody, and the constant region, by well-known methods.

Antibodies thus obtained, may be purified to homogeneity. Any standard method protein separation and purification method may be used for antibody separation and purification. For example, chromatographies, such as affinity chromatography; filters; ultrafiltration; salting out; dialysis; SDS polyacrylamide gel electrophoresis; isoelectric point electrophoresis; etc. may be appropriately combined to isolate and purify the antibody (Antibodies: A Laboratory Manual. Ed Harlow and David Lane, Cold Spring Harbor Laboratory, 1988). However, the methods are not limited thereto. The concentration of the obtained antibody may be determined by measuring absorbance, by enzyme-linked immunosorbent assay (ELISA), etc.

Columns used for affinity chromatography include, protein A column and protein G column. For example, Hyper D, POROS, Sepharose F. F. (Pharmacia), etc. may be mentioned as columns using protein A columns.

Chromatographies other than affinity chromatography are, for example, ion exchange chromatography, hydrophobic chromatography, gel filtration chromatography, reverse phase chromatography, adsorption chromatography, and so on (Strategies for Protein Purification and Characterization: A Laboratory Course Manual. Ed Daniel R. Marshak et al., Cold Spring Harbor Laboratory Press, 1996). These chromatographies can be conducted using liquid chromatographies, such as HPLC, and FPLC.

For example, measurement of absorbance, enzyme-linked immunosorbent assay (ELISA), enzyme immunoassay (EIA), radioimmunoassay (RIA), or immunofluorescence may be used to measure the antigen binding activity of an antibody of the invention. In ELISA, an antibody of the present invention is immobilized on a plate, a protein of the invention is applied, and then a sample containing a desired antibody, such as culture supernatant of antibody producing cells or a purified antibody, is applied. Then, a secondary antibody labeled with an enzyme such as alkaline phosphatase that recognizes the primary antibody is applied. The plate is then incubated. After washing, an enzyme substrate like p-nitrophenyl phosphate is added to the plate and absorbance measured to evaluate the antigen binding activity of the sample. A fragment of a protein, such as a C-terminus fragment, may be used as the protein. BIAcore (Pharmacia) may be used to evaluate the antigen binding activity of an antibody according to the present invention.

The above methods allow the detection or measurement of a protein of the invention, by exposing an antibody of the invention to a sample assumed to contain the protein of the invention, and detecting or measuring the immune complex formed by the antibody and the protein. Because the method of detection or measurement of a protein according to the invention can specifically detect or measure a protein, the method may be useful in a variety of experiments, in which the protein is used, and in testing Alzheimer's disease or cancer as follows.

The present invention also provides DNAs comprising at least 15 nucleotides that are complementary to a DNA encoding the human SMAP-1 protein (SEQ ID NO: 1) or to the complementary strand thereof.

"Complementary strand" herein refers to one strand of a double strand DNA comprising A:T (or A:U for RNA) and G:C base pairs, when viewed against the other strand. Furthermore, "complementary" means not only a nucleotide sequence completely complementary to a continuous nucleotide sequence with at least 15 nucleotides but also a homology of at least 70%, preferably at least 80%, more preferably 90%, and most preferably 95% or more at the nucleotide sequence level. Homology can be determined using the algorithm described herein.

Such nucleic acids include probes and primers used for the detection and amplification of a DNA encoding a protein of the present invention; probes and primers for detecting the expression of a DNA; nucleotides and nucleotide derivatives (for example, antisense oligonucleotides or DNA encoding ribozymes, or DNAs encoding them, etc.) used for repressing the expression of a protein of the present invention. Furthermore, such nucleic acids can be used in the preparation of DNA chips.

If the DNA is used as a primer, the 3' region thereof may be the complementary site, and restriction enzyme recognition sites, tag sequences, etc. may be attached to the 5' region.

Antisense oligonucleotides comprise, for example, an antisense oligonucleotide that hybridizes with any portion of the nucleotide sequence of SEQ ID NO: 1. The antisense oligonucleotide is preferably an antisense of a continuous sequence comprising at least 15 nucleotides or more within the nucleotide sequence of SEQ ID NO: 1. More preferably, the above continuous sequence comprising at least 15 nucleotides or more and contains a translation initiation codon.

A derivative or modified form of an antisense oligonucleotide may also be used. The latter form may be prepared by modifying an antisense oligonucleotide with lower alkylphosphonates, such as, methylphosphonate or ethylphosphonate, or with phosphorothioate, or phosphoroamidate.

The antisense oligonucleotide is not restricted to one in which all nucleotides are complementary to the corresponding nucleotides within a given region of a DNA or mRNA. So long as it can specifically hybridize with the nucleotide sequences of SEQ ID NO: 1, it may have one or more nucleotide mismatches.

A derivative of an antisense oligonucleotide of the present invention may act on cells producing a protein of the invention and bind to a DNA or mRNA encoding the protein, and then, it may inhibit the expression of the protein of the invention by inhibiting its transcription or translation, or by promoting the degradation of mRNA, and thereby inhibiting the function of the protein.

A derivative of an antisense oligonucleotide of the present invention may be mixed with an appropriate base that is inactive against the derivative, and used as a medicine for external application, such as a salve or poultice.

If necessary, it may be mixed with excipients, isotonizing agents, solubilizing agents, stabilizers, preservatives, painkillers, or the like; and prepared as a tablet, powder, granule, capsule, liposome capsule, injectable solution, liquid formulation, nose drops, freeze-dried agent, etc. The above may be achieved according to standard methods.

For treating patients, a derivative of an antisense oligonucleotide of the present invention may be, for example, directly applied to the affected area of a patient, or administered into blood vessels so as to finally reach the affected area. Moreover, the derivative may be encapsulated in antisense-encapsulating materials, such as liposomes, poly-L-lysine, lipid, cholesterol, lipofectin, or their derivatives in order to increase durability and/or membrane permeability.

Dose of a derivative of the antisense oligonucleotides of the present invention may be appropriately adjusted depending on the patient's conditions, and a favorable amount such as 0.1 to 100 mg/kg, or more, preferably 0.1 to 50 mg/kg, may be administered.

Since the antisense oligonucleotides of the present invention inhibit the expression of a protein of the invention, they are useful as an inhibitor of the biological activity of the protein of the invention. An expression inhibitor comprising an antisense oligonucleotide of the present invention is useful due to its ability to inhibit the biological activity of a protein of the invention.

A protein of the invention may be useful for screening a compound that binds to the protein. Specifically, the protein may be used in a method of screening for a compound, which comprises the steps of exposing the protein of the present invention to a test sample expected to contain a compound binding to the protein, and selecting a compound having the activity of binding to the protein.

Proteins of the invention used for screening may be recombinant or natural proteins, or partial peptides. Alternatively, they may be in the form expressed on the surface of a cell, or in the form of a membrane fraction. Samples tested include, but are not limited to, cell extracts, cell culture supernatants, products of fermentation microorganisms, marine organism extracts, plant extracts, purified or crude preparations of proteins, peptides, non-peptide compounds, synthetic low-molecular weight compounds, and natural compounds. A protein of the present invention to be contacted with a test sample may be brought into contact with the test sample, as a purified protein, as a soluble protein, in the form attached to a carrier, a fusion protein with other proteins, in the form expressed on the cell membrane, or as a membrane fraction.

Various methods known to those skilled in the art may be used as the screening method of, for example, a protein that binds to a protein of the present invention using a protein of the present invention. Such a screening can be carried out, for example, by the immunoprecipitation method. Specifically, the method can be carried out as follows. A gene encoding a protein of this invention is expressed by inserting the gene into vectors for foreign gene expression, such as pSV2neo, pcDNA I, and pCD8; and expressing the gene in animal cells, etc. Any generally used promoter may be employed for the expression, including the SV40 early promoter (Rigby In Williamson (ed.), Genetic Engineering, Vol. 3. Academic Press, London, p.83–141 (1982)), EF-1α promoter (Kim, et al. Gene 91, p. 217–223 (1990)), CAG promoter (Niwa, et al. Gene 108, p. 193–200 (1991)), RSV LTR promoter (Cullen, Methods in Enzymology 152, p.684–704 (1987)), SR α promoter (Takebe et al., Mol. Cell. Biol. 8, p.466 (1988)), CMV immediate early promoter (Seed and Aruffo Proc. Natl. Acad. Sci. USA 84, p. 3365–3369 (1987)), SV40 late promoter (Gheysen and Fiers J. Mol. Appl. Genet. 1, p.385–394 (1982)), Adenovirus late promoter (Kaufman et al., Mol. Cell. Biol. 9, p.946 (1989)), HSV TK promoter, etc.

Transfer of a foreign gene into animal cells for the expression therein can be performed by any of the following methods, including the electroporation method (Chu, G. et al., Nucl. Acid Res. 15, 1311–1326 (1987)), the calcium phosphate method (Chen, C. and Okayama, H. Mol. Cell. Biol. 7, 2745–2752 (1987)), the DEAE dextran method (Lopata, M. A. et al. Nucl. Acids Res. 12, 5707–5717 (1984); Sussman, D. J. and Milman, G. Mol. Cell. Biol. 4, 1642–1643 (1985)), the lipofectin method (Derijard, B. Cell. 7, 1025–1037 (1994); Lamb, B. T. et al. Nature Genetics 5, 22–30 (1993)), Rabindran, S. K. et al. Science 259, 230–234 (1993)), etc.

A protein of this invention can be expressed as a fusion protein having a recognition site for a monoclonal antibody whose specificity has been established by introducing the recognition site (epitope) into the N- or C-terminus of a protein of this invention. For this purpose, a commercial epitope-antibody system can be utilized (Jikken Igaku (Experimental Medicine) 13, 85–90 (1995)). Vectors that express fusion proteins via a multi-cloning site with β-galactosidase, maltose-binding protein, glutathione S-transferase, green fluorescence protein (GFP), etc., are commercially available.

To minimize alteration in properties of a protein of this invention due to fusion protein formation, a method for preparing a fusion protein has been reported that involves introducing only a small epitope portion comprising several to dozens amino acid residues. For example, the epitopes of polyhistidine (His-tag), influenza hemagglutinin (HA), human c-myc, FLAG, Vesicular stomatitis virus glycoprotein (VSV-GP), T7 gene 10 protein (T7-tag), human herpes simplex virus glycoprotein (HSV-tag), E-tag (epitope on the monoclonal phage), etc., and monoclonal antibodies to recognize these epitopes can be utilized as the epitope-antibody system for screening proteins binding to the protein of this invention (Jikken Igaku (Experimental Medicine) 13, 85–90 (1995)).

For immunoprecipitation, immune complexes are formed by adding these antibodies to the cell lysate prepared using suitable detergents. This immune complex comprises a protein of this invention, a protein binding to the protein, and an antibody. The immunoprecipitation can be also performed using an antibody to a protein of this invention, besides antibodies to the above-described epitopes. An antibody against a protein of this invention can be prepared by, for example, inserting a gene encoding a protein of this invention into an appropriate expression vector of E. coli to express it in the bacterium, purifying the protein thus expressed, and immunizing rabbits, mice, rats, goats, chicken, and such, with the purified protein. The antibody can also be prepared by immunizing the above-described animals with partial peptides of a protein of this invention.

Immune complexes can be precipitated using, for example, Protein A Sepharose and Protein G Sepharose when the antibody is a murine IgG antibody. In addition, when the protein of this invention is prepared as a fusion protein with the epitope of, for example, GST, and such, the immune complex can be formed using a substance that specifically binds to these epitopes, such as glutathione-Sepharose 4B, giving the same result as in the case where the antibody for the protein of this invention is used.

Immunoprecipitation, in general, may be carried out according to, or following the method described in literature (Harlow, E. and Lane, D.: Antibodies, pp.511–552, Cold Spring Harbor Laboratory publications, New York (1988)).

SDS-PAGE is generally used -for the analysis of immunoprecipitated proteins. Bound proteins can be analyzed based on the molecular weights of proteins using a gel of an appropriate concentration. In this case, although proteins bound to a protein of this invention, are in general hardly detectable by the usual protein staining method, such as Coomassie staining and silver staining, the detection sensitivity can be improved by culturing cells in a medium containing radio isotope-labeled $^{35}$S-methionine and $^{35}$S-cysteine to label proteins inside the cells, and detecting the labeled proteins. Once the molecular weight of a protein is determined the desired protein can be purified directly from SDS-polyacrylamide gel and then sequenced.

Isolation of a protein that binds to a protein of the present invention using the protein may be carried out via West-Western blotting method (Skolnik E. Y. et al. (1991) Cell 65: 83–90). Specifically, a cDNA library is constructed from cells, tissues, or organs (for example, liver or kidney) in which a protein binding to a protein of the present invention is expected to be expressed, by using phage vectors (λgt11, ZAP, etc.). Then, this is expressed on LB-agarose, transferred to a filter membrane, which is reacted with a purified labeled protein of the invention. The plaques expressing proteins that bind to the protein of the invention can be identified by detecting the label. The protein of the invention may be labeled by a method utilizing the binding between biotin and avidin, or a method utilizing an antibody that specifically binds to the protein of the present invention, or a peptide or polypeptide (e.g., GST and such) that is fused to the protein of the present invention. Methods using radioisotope or fluorescence and such may also be used.

Alternatively, according to another embodiment of the method for screening of the present invention, a two-hybrid system utilizing cells may be used (Fields S. and Sternglanz R. (1994) Trends Genet. 10: 286–292; Dalton S. and Treisman R. (1992) "Characterization of SAP-1, a protein recruited by serum response factor to the c-fos serum response element." Cell 68: 597–612; "MATCHMAKER Two-Hybrid System", "Mammalian MATCHMAKER Two-Hybrid Assay Kit", "MATCHMAKER One-Hybrid System" (products of Clontech); "HybriZAP Two-Hybrid Vector System" (Stratagene)). The two-hybrid system can be used as follows: (1) a protein of the present invention or a partial peptide thereof is fused to the SRF DNA binding region or GAL4 DNA binding region and expressed in yeast cells; (2) a cDNA library, which expresses proteins as fusion proteins with VP16 or GAL4 transcription activating regions, is prepared from cells expected to express proteins binding to the protein of the present invention; (3) the library is introduced to above mentioned yeast cells; and (4) library-derived cDNA are isolated from the positive clones detected (positive clones can be confirmed by activation of reporter genes due to the binding of the present protein and the binding protein expressed in the yeast cell). The protein encoded by the cDNA can be obtained by introducing the isolated cDNA into $E.$ $coli$ and expressing it. Thus, a protein binding to a present protein or genes thereof can be prepared. For example, in addition to the HIS3 gene, Ade2 gene, LacZ gene, CAT gene, luciferase gene, PAI-1 (Plasminogen activator inhibitor type1) gene, and so on, can be mentioned as reporter genes used in the 2-hybrid system, but are not restricted thereto. The screening using the two-hybrid system can be also carried out using mammalian cells besides yeast.

Alternatively, a compound binding to a protein of the present invention can be screened by affinity chromatography. For example, a protein of the invention is immobilized on a carrier of an affinity column and a test sample, in which a protein binding to the protein of the invention is predicted to be expressed, is applied to the column. The test sample used herein may be a cell extract, cell lysate, etc. After loading the test sample, the column is washed, and proteins bound to the protein of the invention can be obtained.

The DNA encoding the protein may be obtained by analyzing the amino acid sequence of the obtained protein, synthesizing oligo DNA based on the sequence information, and screening a cDNA library using the DNA as the probe.

A biosensor utilizing the surface plasmon resonance phenomenon may be used as a means for detecting or measuring a compound bound in the present invention. When such a biosensor is used, the interaction between a protein of the invention and a test compound can be observed at real-time as a surface plasmon resonance signal, using only a minute amount of proteins without labeling (for example, BIAcore, Pharmacia). Therefore, it is possible to evaluate the binding between a protein of the invention and a test compound using a biosensor like BIAcore.

In addition, methods for isolating not only proteins, but also compounds (including agonists and antagonists) binding to the proteins of the invention are known in the art. Such methods include, for example, the method of screening for a binding molecule by contacting synthesized compounds or natural substance banks, or random phage peptide display libraries with an immobilized protein of the invention, and the high-throughput screening method using the combinatorial chemistry techniques (Wrighton, N. C., Farrell, F. X., Chang R., Kashyap A. K., Barbone F. P., Mulcahy L. S., Johnson D. L., Barrett R. W., Jolliffe L. K., and Dower W. J., "Small peptides as potent mimetics of the protein hormone erythropoietin" Science (UNITED STATES), Jul. 26, 1996, 273 p458–64; Verdine G. L., "The combinatorial chemistry of nature" Nature (ENGLAND), Nov. 7, 1996, 384, p11–13; Hogan J. C. Jr., "Directed combinatorial chemistry" Nature (ENGLAND) Nov. 7, 1996, 384, p17–9).

A compound that can be isolated by the screening of the present invention may serve as a candidate for a drug that can regulate the activity of the protein, and thus may be applied for the treatment of diseases caused by an abnormal expression, function, etc. of the protein. Such a drug may also be applied against diseases that may be treated by regulating the activity of a protein of the present invention. Compounds, which are isolated by the screening method of this invention whose partial structure is modified by addition, deletion and/or substitution, are also included in compounds that bind to the proteins of this invention.

When using a protein of this invention or a compound that can be isolated by the screening of this invention as a pharmaceutical agent for humans and other animals, such as, mice, rats, guinea-pigs, rabbits, chicken, cats, dogs, sheep, pigs, cattle, monkeys, baboons, and chimpanzees, the protein or the isolated compound can be directly administered or can be formulated using known pharmaceutical preparation methods. For example, according to the need, the drugs can be taken orally as sugarcoated tablets, capsules, elixirs, and microcapsules; or non-orally in the form of injections of sterile solutions or suspensions with water or any other pharmaceutically acceptable liquid. For example, the compounds can be mixed with pharmacologically acceptable carriers or medium, specifically, sterilized water, physiological saline, plant-oil, emulsifiers, solvents, surfactants, stabilizers, flavoring agents, excipients, vehicles, preservatives, and binders, in a unit dose form required for generally accepted drug implementation. The amount of active ingredients in these preparations makes a suitable dosage within the indicated range acquirable.

Examples of additives that can be mixed to tablets and capsules are, binders, such as gelatin, corn starch, tragacanth gum, and arabic gum; excipients, such as crystalline cellulose; swelling agents, such as corn starch, gelatin, and alginic acid; lubricants, such as magnesium stearate; sweeteners, such as sucrose, lactose, and saccharin; flavoring agents, such as peppermint, Gaultheria adenothrix oil, and cherry. When the unit dosage form is a capsule, a liquid carrier, such as oil, can also be included in the above ingredients. Sterile composites for injections can be formulated following normal drug implementations using vehicles, such as distilled water used for injections.

Physiological saline, glucose, and other isotonic liquids including adjuvants, such as D-sorbitol, D-mannnose, D-mannitol, and sodium chloride, can be used as aqueous solutions for injections. These can be used in conjunction with suitable solubilizers, such as alcohol, specifically ethanol, polyalcohols such as propylene glycol and polyethylene glycol; non-ionic surfactants, such as Polysorbate 80 (TM), and HCO-50.

Sesame oil or Soy-bean oil can be used as a oleaginous liquid and may be used in conjunction with solubilizers, such as benzyl benzoate and benzyl alcohol; may be formulated with buffer, such as phosphate buffer and sodium acetate buffer; pain-killers, such as procaine hydrochloride; stabilizers, such as benzyl alcohol, phenol; and anti-oxidants. The prepared injection is filled into a suitable ampule.

Methods well known to those skilled in the art may be used to administer a pharmaceutical compound to patients, for example as intraarterial, intravenous, subcutaneous injections, and also as intranasal, transbronchial, intramuscular, percutaneous, or oral administrations. The dosage varies according to the body-weight and age of a patient, and the administration method, but one skilled in the art can suitably select the dosage. If said compound can be encoded by a DNA, the DNA can be inserted into a vector for gene therapy to perform the therapy. The dosage and method of administration vary according to the body-weight, age, and symptoms of a patient, but one skilled in the art can select them suitably.

The dose of a protein of the invention may vary depending on the subject, target organ, symptoms, and administration method, but is generally, about 100 µg to 20 mg per day for a normal adult (body weight: 60 kg).

Although varying according to the symptoms, the dose of a compound that binds to a protein of this invention or a compound that inhibits the activity of the protein are considered generally in the range of about 0.1 to 100 mg, preferably about 1.0 to 50 mg, and more preferably about 1.0 to 20 mg per day for adults (body weight: 60 kg) in the case of an oral administration.

Although varying according to the subject, target organ, symptoms, and method of administration, a single dose of a compound for parenteral administration is preferably considered to be, for example, when administered intravenously to normal adults (60 kg body weight) in the form of injection, in the range of about 0.01 to 30 mg, preferably about 0.1 to 20 mg, and more preferably about 0.1 to 10 mg per day. Doses converted to 60 kg body weight or per body surface area can be administered to other animals.

BRIEF DESCRIPTION OF THE DRAWINGS

FIG. 1 depicts the nucleotide sequence of human SMAP-1 cDNA and the deduced amino acid sequence thereof. The predicted signal sequence is underlined.

FIG. 2 depicts the comparison of nucleotide sequences between human SMAP-1 and SDF2. Identical nucleotide residues between the two are marked with "★".

FIG. 3 is a continuation of FIG. 2.

FIG. 4 depicts the comparison of amino acid sequences between human SMAP-1 and SDF2. Identical amino acid residues between the two are marked with "★".

BEST MODE FOR CARRYING OUT THE INVENTION

Figure 5:
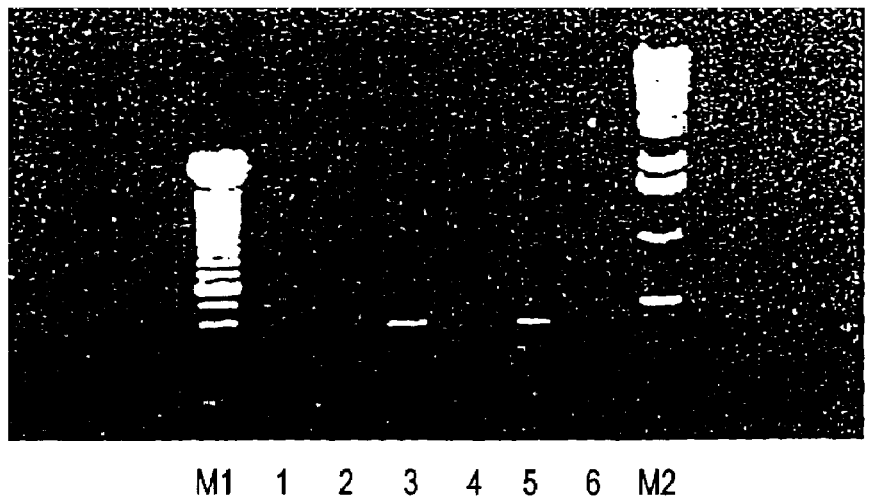
FIG. 5 depicts an electrophoretogram demonstrating the result of RT-PCR analysis of the expression of SMAP-1 in various human tissues and cell lines. M1, 100-bp ladder marker; 1, brain; 2, heart; 3, liver; 4, spleen; 5, kidney; 6, lymphocytes; M2, 1-kbp ladder marker. The samples were electrophoresed on a 1.2% agarose gel, and then were stained with ethidium bromide.

The present invention is illustrated in detail below with reference to Examples, but is not to be construed as being limited thereto.

EXAMPLE 1

Preparation of Human Fetal Liver cDNA Library

Human fetal liver cDNA library was prepared by synthesizing cDNA from human fetal liver polyA$^+$. mRNA (Clontech) and inserting them into TMT expression vector pTMT-shPM1-kappa. The cDNA library was prepared using cDNA synthesis kit (STRATAGENE) basically according to the protocol attached to the kit from STRATAGENE, with the following modifications. Superscript II from GIBCO-BRL was used as the reverse transcriptase. A HindIII-SmaI adapter from Takara was used as the adapter that was attached to the 5'-end of cDNA. An improved oligo dT primer was used for the first strand cDNA synthesis. The primer sequence is shown in SEQ ID NO: 3. Specifically, the synthesized cDNA was inserted at the HindIII/BamHI site in the sense orientation into the TMT expression vector using the oligo dT primer to which a BamHI site was added. Further, a termination codon was inserted in three frames immediately upstream of the TTT . . . TTT sequence of the oligo dT primer. This modification prevents the unwanted translation, even if the cDNA has been inserted in reverse orientation into the TMT expression vector. Size sep 400 Spun Column from Pharmacia Biotech was used as size fractionation column.

Specific method for preparing the cDNA library was as follows. Five microgram mRNA as the starting material, first, the first strand cDNA was synthesized from the polyA tail at the 3'-end using the above primer and reverse transcriptase (GIBCO-BRL; Superscript II). Then, the second strand cDNA synthesis was carried out using DNA polymerase, and both ends of the cDNA were blunted. The HindIII-SmaI adapter (Takara) was added to both ends. The 3'-end of the cDNA was digested with BamHI. Then, size fractionation was carried out (Pharmacia Biotech; Size sep 400 Spun Column) to remove cDNA fragments of 0.4-kb or shorter. The cDNA was recovered and inserted at the HindIII-BamHI site of TMT expression vector shPM1-kappa. The vector was introduced into E. coli DH10B (GIBCO-BRL; Electro Max DH10B) by electroporation to prepare the human fetal liver cDNA library.

The cDNA library was aliquoted; each pool contained $2 \times 10^5$ clones. Five pools (pool Nos: 1–5) out of them were subjected to screening by the TMT method.

EXAMPLE 2

Screening of the Human Fetal Liver cDNA Library Using the TMT Method (1) Introduction of Genes into COS-7 Cells (First Round)

Four microgram of each of the plasmid DNAs prepared from the respective pools (pool Nos: 1–5) was used for transfecting COS-7 cells using FuGENE™6 (Boehringer-Mannheim).

Specifically, a day before transfection, COS-7 cells were plated in three 100-mm dishes (Falcon; 3003) at a cell density of $1 \times 10^6$ cells/dish. The cells were cultured overnight in 10 ml DMEM medium (GIBCO-BRL) containing 10% fetal calf serum at 37° C. under 5% $CO_2$. On the day of transfection, 12 µl of FuGENE™6 was added to 0.2 ml of serum-free DMEM medium and was incubated at room temperature for 5 minutes, and 4 µg plasmid DNA was mixed thereto followed by incubation at room temperature for 15 min. The mixture was added to the above-mentioned COS-7 cells. The cells were cultured at 37° C. under 5% $CO_2$ for three days.

(2) Preparation of Panning Dish

Panning dishes coated with goat anti-mouse IgG antibody (DAINIPPON PHARMACEUTICAL; goat anti-mouse IgG (H+L chains)) were prepared according to the method described in the literature (Seed, B. et al., Proc. Natl. Acad. Sci. USA. (1987) 84, 3365–3369). Specifically, the goat anti-mouse IgG antibody was added to 50 mM Tris-HCl (pH 9.5) at a final concentration of 10 µg/ml. 3-ml aliquots of the prepared antibody solution were added to dishes with a diameter of 60 mm (Falcon; dish 1007) (60-mm dish), and the dishes were incubated at room temperature for 3 hours. The dishes were washed 3 times with a solution of 0.15 M NaCl, and then PBS containing 5% fetal calf serum, 1 mM EDTA, and 0.02% NaN$_3$ was added thereto for blocking, and the dishes were used for panning as described below.

(3) Panning

The transfected COS-7 cells as described above were harvested with PBS containing 1 mM EDTA, and washed once with PBS containing 5% fetal calf serum. Then, the cells were suspended in FACS buffer (PBS containing 2% fetal calf serum and 0.05% NaN$_3$). Soluble IL-6R was added at a concentration of 0.5 µg/10$^6$ cells to the cell suspensions, and incubated on ice for 90 minutes. Then, the cells were washed twice with FACS buffer, and resuspended in fresh FACS buffer. The mouse anti-IL-6 receptor antibody MT-18 was added at a concentration of 0.35 µg/10$^6$ cells to the cell suspension, and incubated on ice for 30 minutes. The cells were washed twice with FACS buffer, and then suspended in 2 ml PBS containing 5% fetal calf serum and 0.02% NaN$_3$. The cell suspension was added to the panning plates that were coated with the goat anti-mouse IgG antibody.

The above-mentioned COS-7 cells were incubated on the panning plates at room temperature for about 2 hours, and gently washed 3 times with PBS containing 5% fetal calf serum and 0.02% NaN$_3$. Plasmid DNAs were recovered from the cells immobilized on the panning plates using Hirt's solution (solution containing 0.6% SDS and 10 mM EDTA). Forty microliter of E. coli DH10B (GIBCO-BRL; Electro Max DH10B) was transfected with the half of the recovered plasmid DNA by electroporation, and was cultured in 1 ml of SOC medium at 37° C. for 1 hour. Then, an aliquot was taken for titer check on LB-plate containing 100 µg/ml ampicillin (Meiji Seika)/30 µg/ml kanamycin (Wako Pure Chemical Industries). On the other hand, the remaining E. coli was transferred into 500 ml of LB-liquid medium containing the same concentration of ampicillin/kanamycin and cultured at 37° C. overnight. Then, aliquots were sampled from the culture, DMSO was added thereto at a final concentration of 7%, and were stored frozen 1 ml/tube at −80° C.

(4) Introduction of Genes into COS-7 Cells (Second Round)

To enrich positive clones (cDNA clones encoding transmembrane domains), the second and subsequent gene transfer to COS cells were carried out byprotoplast fusion (Sandri-Goldrin. et al., Mol. Cell. Biol. (1987) 1, 743–752). Specifically, the E. coli were taken from a tube of the frozen stock prepared as described above and cultured in 500 ml liquid medium of LB-ampicillin (100 µg/ml)/kanamycin (30 µg/ml) at 37° C. When the O.D. at 600 nm reached 0.5, chloramphenicol (Wako Pure Chemical Industries) was added to the culture at a final concentration of 150 µg/ml to suppress the growth of E. coli and to enhance DNA synthesis. The cells were further incubated at 37° C. overnight. Bacterial cells were harvested from 100-ml culture, and suspended in 5 ml of an ice-cold buffer of20% sucrose/50 mM Tris-HCl (pH 8). 1 ml of 5 mg/ml lysozyme (Sigma) was added to the suspension, and then was allowed to stand still on ice for 5 minutes. 2 ml of 0.25 M EDTA was added thereto, and was further allowed to stand still on ice for 5 minutes. Then, 2 ml of 50 mM Tris-HCl buffer (pH 8) was added to the mixture, incubated at 37° C. for 5 minutes, and then transferred onto ice. 20 ml of ice-cold 10% sucrose/10 mM magnesium chloride/DMEM was added, and the mixture was stirred well. The E. coli protoplasts thus prepared were fused with COS cells to transfer the gene.

Specifically, COS cells were plated in six 60-mm dishes at a concentration of 1×10$^5$ cells/dish and cultured for 3 days. The culture medium was discarded, and 5-ml aliquots of the suspension of the E. coli protoplasts prepared as described above were added to the dishes. The dishes were placed in swing baskets, and centrifuged at 2,000 rpm at room temperature for 10 minutes. After aspirating the supernatant, 1.5 ml solution of 50% polyethylene glycol 1500 (Wako Pure Chemical Industries; PEG1540)/DMEM was thoroughly poured on each dish, and immediately thereafter, the dishes were tilted to aspirate off the excess polyethylene glycol solution. The dishes were then washed with a DMEM solution. 5 ml of DMEM medium containing 50 µg/ml gentamicin (GIBCO-BRL) and 10% fetal calf serum was added to the dishes, and were incubated at 37° C. for 5 hours. The culture medium was replaced with fresh one, and was further incubated at 37° C. for three days. The COS cells fused with protoplast were harvested with PBS containing 1 mM EDTA, and then washed once with PBS containing 5% fetal calf serum. The cells were suspended in FACS buffer (PBS containing 2% fetal calf serum and 0.05% NaN$_3$) and subjected for panning for the second time. DNA was recovered from the panning plate, and then subjected to the third-round of gene transfer to COS-7 cells.

(5) Introduction of Genes into COS-7 Cells (Third Round)

Gene transfer into COS-7 cells was carried out for the third time (third-round) by the same protoplast fusion method as described above. Panning was also carried out for the third time according to the same procedure as described above.

EXAMPLE 3

Analysis of the Nucleotide Sequence of Clone HFL0304h Isolated by the TMT Method and the Deduced Amino Acid Sequence Thereof After panning for the third time, colonies were randomly chosen from the plate for titer check from pool No. 5, cultured in 2 ml of liquid medium of LB-ampicillin (100 µg/ml) at 37° C., and the plasmid DNAs were prepared. Then, clones containing the appropriate insert sequence of interest were selected by an analysis using restriction enzymes, SmaI and BamHI, to determine the nucleotide sequences from the 5'-end sequence.

The obtained nucleotide sequences and the deduced amino acid sequences thereof were subjected to database search (BLAST-N and BLAST-P) in public databases (GenBank and SWISSPROT) to narrow the list of candidate sequences with novelty. In addition, the obtained amino acid sequences were analyzed to possess transmembrane domains by analysis software SOSUI. SOSUI is a computer program to predict transmembrane domains from protein primary structures, which was developed by professor Mitaku at Tokyo University of Agriculture and Technology. Further, known secretory sequences were obtained in the Example herein, and by examining these sequences, SOSUI was demonstrated to sometimes predict a signal sequences as a transmembrane domain.

The result of the above-mentioned database search revealed clone HFL0304 h as a novel gene whose sequence was not shared by any of the sequences deposited in GenBank and SWISSPROT. Further, it was demonstrated that the N-terminal amino acid sequence deduced from the obtained clone contained a sequence recognized as a transmembrane domain by SOSUI. According to a more detailed database search, the clone was demonstrated to be a novel gene exhibiting high homology at the nucleotide sequence and amino acid sequence levels (50.9% and 60.09%, respectively) to human stromal cell-derived factor-2 (SDF-2) located on chromosome 22. This result was obtained as follows:

First, an early BLAST search revealed information as follows:

1) No entry of a nucleotide sequence completely matching with the nucleotide sequence of clone HFL0304h could be detected in the GenBank database;

2) No entry of an amino sequence completely matching with the amino acid sequence deduced from the clone HFL0304h could be detected in the SWISSPROT database;

3) The clone HFL0304h exhibited high homology to SDF-2 at both the nucleotide sequence and amino acid sequence levels.

4) The clone HFL0304h exhibited high homology to the sequence deposited as U.S. Pat. No. 5,576,423 at the nucleotide sequence level.

5) The clone HFL0304h exhibited high homology to yeast protein mannosyltransferase at the amino acid sequence level.

Based on these findings, further analyses were carried out.

The nucleotide sequence described in U.S. Pat. No. 5,576,423 is that of SLAM2 cDNA which is a splice variant of SLAM1. A part of the nucleotide sequence of the clone HFL0304h is identical to the nucleotide sequence downstream of the 1040th nucleotide from the 5'-end of SLAM2 (the 3'-untranslated region of SLAM2 cDNA). However, the 5'-end nucleotide sequence of the clone HFL0304h was apparently different from that of SLAM2, and the nucleotide sequence of HFL0304h encoded a very long amino acid sequence (219 amino acid residues). Thus, the sequence was searched again in databases containing the latest entry data. The result newly revealed that the nucleotide sequence of the clone HFL0304h was identical to that of a genomic DNA (accession number: AP000553) on chromosome 22; which also suggested the exon-intron organization of the genome sequence. According to the description of U.S. Pat. No. 5,576,423, both of the SLAM1 and SLAM2 genes are located on chromosome 1. However, clone HFL0304h was confirmed to be located on chromosome 22, which raises the possibility that the clone HFL0403h is a different gene from SLAM2. Thus, database search was carried out using SLAM2 as a query against a database covering chromosomes 1 and 22 in the Sanger Center. Although SLAM2 was demonstrated to be present on chromosome 1, no locus exhibiting high homology to the clone HFL0304h could be detected on chromosome 1, but on chromosome 22. These findings suggest the possibility that the SLAM2 cDNA described in U.S. Pat. No. 5,576,423 is an artifact generated by the fusion of the original SLAM2 gene on chromosome 1 and the HFL0304h gene on chromosome 22. Such artifacts are often produced during cDNA library construction.

According to the results of the above analysis, clone HFL0304h was demonstrated not to be the 3'-untranslated region of SLAM2 cDNA but a novel gene, which is actually located on chromosome 22, encoding a protein having homology to human SDF-2.

EXAMPLE 4

Full-Length Cloning of SDF2 Homologue, HFL0304h, by 5' RACE Method

According to the result of nucleotide sequence analysis, the clone HFL0304h was suggested to be an incomplete (non full-length) clone due to the fact that it had a polyA tail at the 3'-end but not a putative translation initiation codon at the 5'-end. Thus, the present inventors tried to isolate the full-length clone by 5' RACE method.

The 5' RACE method was performed with 5' RACE kit (Clontech; SMART™ RACE cDNA Amplification kit). Specifically, primary cDNA was synthesized from 500 ng polyA$^+$ mRNA, which was derived from human fetal liver using oligo dT primer attached to the kit. Then, PCR was conducted with primers specific to the clone HFL0304h using the primary cDNA as the template. More specifically, a reaction solution with a final volume of 25 μl containing 1.25 μl of the primary cDNA, 2.5 μl of 10× PCR buffer, 5 μl Q-solution, 0.125 μl Taq polymerase, 0.5 μl dNTP mixture, 2.5 μl specific primer (attached to SMART RACE kit), 0.5 μl of 10 μM HFL0304h-specific primer (HFL0304HR3; SEQ ID NO: 4), and 12.625 μl of DDW, was prepared to conduct PCR on thermal cycler ABI 2400 with the following condition. Primary denaturation was carried out at 95° C. for 2 minutes, followed by 30 cycles of three-step PCR (at 94° C. for 30 seconds; at 60° C. for 30 seconds; at 72° C. for 30 seconds), and finally, extension reaction at 72° C. for 7 minutes to terminate the primary PCR. In the next step, the PCR products were diluted 10 times, and secondary PCR was conducted with nested primer (attached to SMART RACE kit) and a HFL0304h-specific primer (HFL0304HR4; SEQ ID NO: 5) using a 1-μl aliquot of the products as the template. Specifically, the secondary PCR was carried out in a reaction solution containing 1 μl of the primary PCR solution, 2.5 μl of 10× PCR buffer, 5 μl Q-solution, 0.125 μl Taq polymerase, 0.5 μl dNTP mixture, 0.5 μl nested primer (attached to SMART RACE kit), 0.5 μl of 10 μM HFL0304h-specific primer (HFL0304HR4, SEQ ID NO: 5), and 14.875 μl of DDW, with a final volume of 25 μl. The secondary PCR was also carried out on the ABI 2400 under the same condition as the primary PCR. The products amplified in the secondary PCR were analyzed by electrophoresis on 1.2% agarose gel. A single band of about 250 bp was detected by ethidium bromide staining. Then, the reaction solution of the secondary PCR was purified by spin column analyzed by direct sequencing using primer HFL0304HR4 on ABI7700 DNA sequencer. The full-length sequence was determined by assembling the resulting 5'-upstream sequence and HFL0304h. This gene was dubbed SMAP-1 (FIG. 1).

EXAMPLE 5

The Full-length SMAP-1 Nucleotide Sequence and Comparison with SDF2 at the Nucleotide Sequence and Amino Acid Primary Sequence Level The resulting full-length SMAP-1 nucleotide sequence consisted of 870 bp. Based on the result of amino acid sequence analysis, the full-length clone was estimated to encode 221 amino acid residues. The deduced amino acid sequence was analyzed by PSORT, which is a computer program for predicting the localization of expressed proteins in cells, and was predicted to have a signal sequence consisting of 28 amino acid residues that may be cleaved from the N terminus. The nucleotide sequence of SMAP-1 and the deduced amino acid sequence thereof are shown in FIG. 1.

Further, matching analysis using GENETYX-MAC8.0 revealed that SMAP-1 exhibit 50.09% and 60.09% homology to SDF2 at the nucleotide and amino acid sequence levels, respectively. The comparison of the nucleotide sequence is shown in FIGS. 2A and 2B, and that of the amino acid sequence in FIG. 3.

EXAMPLE 6

Chromosomal Localization of SMAP-1 and Exon-intron Organization Thereof

A sequence corresponding to SMAP-1 was contained in the sequence AP000553 (164946 bp) on chromosome 22q11.2 already deposited in the GenBank, which revealed the exon-intron organization of SMAP-1. According to the numbering of nucleotides shown in FIG. 1, the segment from the first to the 214 bp corresponds to exon 1; the segment of 215–411 bp to exon 2; and the segment 412–816 bp to exon 3.

EXAMPLE 7

Expression of SMAP-1 in Various Human Tissues and Cell Lines

To obtain information on the expression frequency of SMAP-1, specific PCR primers for amplification of SMAP-1 were designed (HFL0304HF and HFL0304HR; SEQ ID NOs: 6 and 7, respectively) to analyze the expression frequency by RT-PCR. Commercially available Multiple Choice First-Strand cDNA set (Nippon Gene) was used as the template for PCR. The PCR reagents and reaction condition were the same as in Example 4 (full-length cloning of the SDF2 homologue HFL0304h by 5' RACE method). The analysis was carried out using, as the templates, the primary cDNAs derived from 6 types of human samples (brain, heart, liver, spleen, kidney, and lymphocytes) contained in the above-mentioned set CH-1101. Consequently, as shown in FIG. 4, all the samples tested were found to express SMAP-1 (by enzyme treatment with BamHI, the amplified gene fragment (394 bp) were verified not to contain any contaminants, e.g., fragments derived from SDF-2, and so on). Particularly strong expression of the gene was observed in liver and kidney.

INDUSTRIAL APPLICABILITY

The present invention provides SMAP-1 gene encoding a novel protein containing a signal sequence. According to the result of the expression pattern, SMAP-1 was considered to be an important molecule involved in the development and maintenance of living cells. Furthermore, the structural properties of the protein suggest that SMAP-1 may function as a glycosyltransferase, participates in the growth and differentiation of hemocytes, and in the differentiation and maturation of sperm. As described above, the protein encoded by the SMAP-1 gene is predicted to be an important molecule in living cells, and thus is a useful target for drug development. Moreover, compounds regulating the function of SMAP-1 are expected to be applicable as pharmaceuticals.

The invention claimed is:

1. An isolated or recombinant nucleic acid selected from the group consisting of (a) SEQ ID NO;1; (b):
 a nucleic acid comprising a sequence complementary to full length of (a).

2. A vector comprising the nucleic acid of claim 1.

3. An isolated host cell transformed with the nucleic acid of claim 1.

4. A method for producing a protein encoded by a nucleic acid comprising SEQ ID NO:1:
 wherein said method comprises the steps of:
 (1) culturing the host cell of claim 3; and
 (2) recovering the expressed protein encoded by the nucleic acid from the host cell or the culture supernatant thereof.

5. An array or DNA chip comprising the isolated or recombinant nucleic acid of claim 1.

6. The host cell of claim 3, wherein the cell is an animal cell, a fungal cell, a plant cell or a bacterial cell.

7. A nucleic acid encoding a fusion protein, wherein the fusion protein comprises the protein encoded by the polynucleotide of claim 1, and another protein or peptide wherein the fusion protein has mannosyltransferase activity.

8. The nucleic acid of claim 7, wherein the other protein or peptide comprises a tag or an antigen fragment.

* * * * *